(12) United States Patent
Miller

(10) Patent No.: US 7,288,246 B2
(45) Date of Patent: Oct. 30, 2007

(54) METHOD OF ALLEVIATING CHRONIC PAIN VIA PERIPHERAL GLUTAMINASE REGULATION

(75) Inventor: Kenneth E. Miller, Sapulpa, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 237 days.

(21) Appl. No.: 10/245,098

(22) Filed: Sep. 13, 2002

(65) Prior Publication Data

US 2003/0072746 A1 Apr. 17, 2003

Related U.S. Application Data

(60) Provisional application No. 60/318,861, filed on Sep. 13, 2001.

(51) Int. Cl.
| | |
|---|---|
| *A61K 38/43* | (2006.01) |
| *A61K 31/385* | (2006.01) |
| *A61K 31/353* | (2006.01) |
| *A61K 31/198* | (2006.01) |
| *A61K 31/20* | (2006.01) |

(52) U.S. Cl. .............. 424/94.1; 514/439; 514/456; 514/558; 514/561

(58) Field of Classification Search .............. 424/94.1; 514/557, 561, 564, 570, 439, 456, 558
See application file for complete search history.

(56) References Cited

U.S. PATENT DOCUMENTS

| | | | |
|---|---|---|---|
| 5,158,976 A * | 10/1992 | Rosenberg | ............. 514/561 |
| 5,552,427 A | 9/1996 | Matsutani et al. | |
| 6,013,672 A | 1/2000 | Ye et al. | |
| 6,248,744 B1 | 6/2001 | Eisenach | |
| 6,291,523 B1 | 9/2001 | Fujimoto et al. | |
| 6,444,665 B1 | 9/2002 | Helton et al. | |

OTHER PUBLICATIONS

Campos, J. A. et al, Involvement of Essential Cysteine and Histidine Residues in the Activity of Isolated Glutaminase from Tumour Cells. Biochim. Biophys. Acta. 1998, vol. 1429, pp. 275-283.*
Kenneth E. Miller et al., "Glutamine-, glutamine synthetase-, glutamate dehydrogenase- and pyruvate caboxylase-immunoreactivities in the rate dorsal root ganglion and peripheral nerve", Brain Research, vol. 945, pp. 202-211, (2002).
Taira et al.; "Effect of intrathecally administered protease inhibitors on the capsaicin-induced nociceptive behavior in mice"; XP002365320 retrived from STN; Database accession No. 127:344461; *abstract* & Annual Report of the Tohoku College of Pharmacy, 43, 139-145, CODEN: TYKNAQ; ISSN: 0495-7342 (1996).

* cited by examiner

*Primary Examiner*—Jon Weber
*Assistant Examiner*—Kailash C. Srivastava
(74) *Attorney, Agent, or Firm*—Dunlap Codding & Rogers

(57) ABSTRACT

A composition having sustained pain-relieving properties such that the composition may be administered to a subject to alleviate chronic pain. The composition includes an effective amount of at least one glutaminase inhibitor. A method for alleviating chronic pain in a subject for an extended period of time is also disclosed, in which the compound is administered to a subject suffering from chronic pain at a site of inflammation such that the administration of the compound results in a reduction in at least one of thermal and mechanical pain responses at the site of inflammation for a period of at least two days without any resulting acute pain behavior. The composition may further include an effective amount of at least one compound having analgesic effects such that the composition also alleviates acute pain.

16 Claims, 22 Drawing Sheets
(1 of 22 Drawing Sheet(s) Filed in Color)

US 7,288,246 B2

METHOD OF ALLEVIATING CHRONIC PAIN VIA PERIPHERAL GLUTAMINASE REGULATION

CROSS-REFERENCE TO RELATED APPLICATIONS

The present application claims benefit under 35 U.S.C. 119(e) of U.S. Ser. No. 60/318,861, filed Sep. 13, 2001, and U.S. Ser. No. 60/411,311, filed Sep. 13, 2002, the contents of which are hereby expressly incorporated herein by reference.

FEDERALLY SPONSORED RESEARCH OR DEVELOPMENT

The government owns certain rights in the present invention pursuant to a grant from the National Institutes of Health, #NS-37361.

BACKGROUND OF THE INVENTION

1. Field of the Invention

The present invention generally relates to methods of alleviating pain, and more particularly, but not by way of limitation, to a method of alleviating chronic pain by regulation of neurotransmitter synthesis.

2. Brief Description of the Related Art

Chronic inflammatory pain is a debilitating condition causing suffering, loss of work and loss of revenue. Several methods of relieving pain from chronic inflammatory conditions such as rheumatoid arthritis, muscle damage, and osteoarthritis are known in the art. However, the prior art methods of relieving pain have several unpleasant or serious side effects and require multiple daily administrations to be effective. For example, narcotics can be used for refractory chronic pain, but administration of narcotics has many side effects, including respiratory depression as well as the possibility of abuse. Additionally, another current method for relief of peripheral pain is topical application of capsaicin cream. This method may be effective for several days but produces severe acute pain in many patients. Further, some pain conditions such as myofascial pain and neuropathies due to nerve injury or disease currently do not have any effective therapies for alleviating pain associated therewith.

Therefore, there exists a need in the art for improved methods of alleviating chronic pain, including pain associated with conditions such as rheumatoid arthritis, muscle damage, osteoarthritis, myofascial pain and neuropathies, which overcome the disadvantages and defects of the prior art methods. It is to such methods of alleviating chronic pain for an extended period of time and with no side effects that the present invention is directed.

SUMMARY OF THE INVENTION

The present invention is related to a method of alleviating chronic pain in a subject for an extended period of time, as well as to a composition having analgesic effects that provides alleviation of chronic pain in a subject for an extended period of time. Briefly, the method of alleviating chronic pain of the present invention includes administration of an effective amount of at least one inhibitor of neurotransmitter synthesis into an inflammatory field. Such inhibitor of neurotransmitter synthesis may be a glutaminase inhibitor.

Pain is a major complication in arthritis and other disorders, and it is difficult to treat effectively for long periods of time. Persistent stimulation of sensory nerves in the area of inflammation is one of the contributors to chronic pain. One stimulator of sensory nerve fibers is glutamate produced by the sensory nerve fibers themselves. Glutamate is a neurotransmitter utilized in signaling by the sensory neurons, and glutamate causes sensitization of surrounding sensory nerves, thereby producing the feeling of pain. The present invention discloses that during experimental arthritis in rats, the sensory nerve cells increase production of glutaminase (GT), the neuronal enzyme that produces glutamate from glutamine. Elevated amounts of glutaminase are shipped to the sensory nerve endings in the skin and joints, thereby causing increased amounts of glutamate to be produced (see FIG. 1). The skin and joints from control rats have little to no detectable glutamate or glutaminase, so this enzyme and neurotransmitter have not been considered previously as possible therapeutic targets for pain relief via peripheral inhibition.

The method of the present invention includes local administration of an effective amount of at least one inhibitor of neurotransmitter synthesis, such as a glutaminase inhibitor, to a subject suffering from chronic pain at a site of inflammation, and the administration of the inhibitor of neurotransmitter synthesis results in a reduction in nociceptive responses, such as thermal and mechanical pain responses, at the site of inflammation for a period of at least two days without any resulting acute pain behavior.

In the experiments described herein, rats were injected in the hindpaw with Complete Freund's adjuvant (heat killed *Mycobacterium*) to create an experimental arthritis. Rats with this type of chronic inflammation have increased sensitivity to pressure and temperature. After several days of inflammation, some rats were injected with a glutaminase inhibitor, such as 6-diazo-5-oxo-L-norleucine (DON), N-ethylmaleimide (NEM), dicoumarol (DC), bromothymol blue (BB) and Palmitoyl Coenzyme A (P-CoA). Following application of the glutaminase inhibitor, the animal's sensitivities to pressure and temperature were brought to more normal values for many days, and these results were seen after only a single injection of the glutaminase inhibitor.

The present invention also includes a method of alleviating both acute and chronic pain in a subject for an extended period of time. The method includes administration of a combination therapy of an effective amount of at least one compound having analgesic effects that provides substantially immediate relief of acute pain in combination with an effective amount of at least one inhibitor of neurotransmitter synthesis to a subject suffering from acute and chronic pain at a site of inflammation. Such combination therapy will provide relief of both acute and chronic pain and results in a substantially immediate reduction of nociceptive responses at the site of inflammation that last for a period of at least two days without any resulting acute behavior.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 14A–C illustrate that ZC levels are modified during chronic inflammation. ZC-immunoreactivity (IR) was examined in the rat $L_4$ DRG during inflammation at an early and later time point (2, 6 days). ZC-IR in DRG neurons of control rats (A) shows a moderate staining of the cytoplasm of all neurons. Following inflammation for 48 hrs, ZC-IR is elevated in the cytoplasm and now appears in the nuclei of many neurons (arrows). ZC-IR remains elevated at 6 days of inflammation and occurs mainly in the cytoplasm although some nuclei (arrows) contain light ZC-IR.

DETAILED DESCRIPTION OF THE INVENTION

Figure 1:
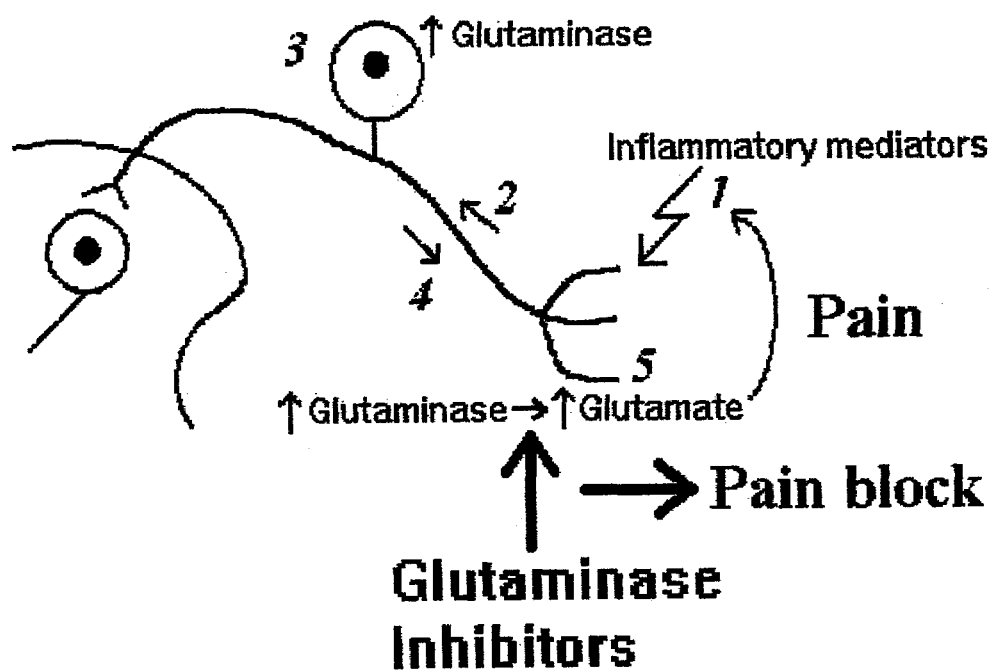
FIG. 1 is a diagrammatic representation of the effects of Glutamate and glutaminase on peripheral sensory nerve stimulation and exacerbation of pain responses.

Before explaining at least one embodiment of the invention in detail, it is to be understood that the invention is not limited in its application to the details of construction and the arrangement of the components or steps or methodologies set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The method of the present invention includes administration of an effective amount of at least one inhibitor of neurotransmitter synthesis to a subject suffering from chronic pain at a site of inflammation. In one embodiment, the inhibitor of neurotransmitter synthesis is a glutaminase inhibitor. The terms "glutaminase inhibitors" or "GT inhibitors" as used herein will be understood to include inhibitors that affect the activity of the glutaminase enzyme, such as inhibitors that may affect binding of glutamine, glutamate or various cofactors to the enzyme. That is, a GT inhibitor may block binding of the substrate glutamine to glutaminase, inhibit release of the product glutamate from glutaminase, or block cofactor binding and therefore slow the catalytic rate of the enzyme. Examples of such GT inhibitors which may be utilized in the method of the present invention include nonspecific inhibitors such as amidotransferase inhibitors and long chain fatty acids. Specific examples of inhibitors of glutaminase activity which may be utilized in the method of the present invention include 6-diazo-5-oxo-L-norleucine (DON), N-ethylmaleimide (NEM), p-chloromercuriphenyl-sulfonate (pCMPS), L-2-amino-4-oxo-5-chloropentoic acid, DON plus o-carbamoyl-L-serine, acivicin [(alphaS,5S)-alpha-amino-3-chloro-4,5-dihydro-5-isoxazoleacetic acid], azaserine, palmitoyl coenzyme A (palmitoyl CoA), stearoyl coenzyme A (stearoyl CoA), bromothymol blue, and combinations or derivatives thereof.

Figure 2:
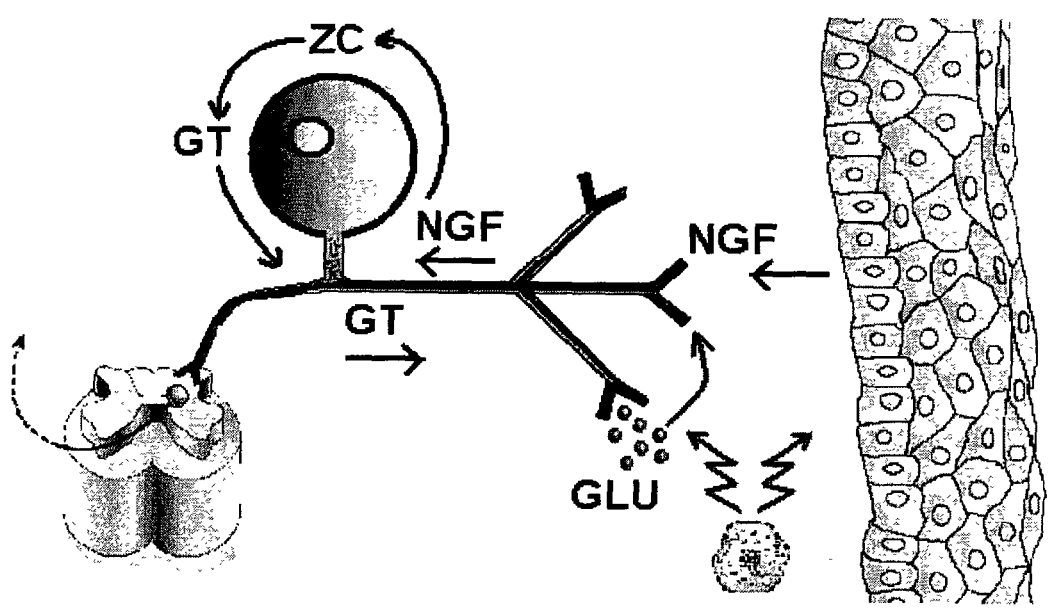
FIG. 2 is a model regarding glutamate production in primary sensory neurons during chronic inflammation. Inflammatory mediators (lightning bolts) activate and sensitize peripheral afferent terminals. This leads to the release of glutamate (GLU) and other substances from peripheral terminals causing further sensitization (arrow). Inflammation stimulates keratinocytes to increase production of nerve growth factor (NGF). NGF is taken up and retrogradely transported to the neuronal cell body where it stimulates increased production of glutaminase (GT). Increased production of GT occurs from stabilization of GT mRNA via zeta-crystallin:quinone oxidoreductase (ZC). Increased amounts of GT are shipped to the periphery causing elevated glutamate production and release, further primary afferent sensitization, and exacerbation of nociceptive responses.

The terms "glutaminase inhibitors" or "GT inhibitors" will also be understood to include inhibitors of glutaminase production. Inhibitors of glutaminase production also include inhibitors of transcription of the gene encoding glutaminase as well as inhibitors of regulatory proteins involved in transcription of the glutaminase gene. Inhibitors of glutaminase production also include inhibitors of translation of the glutaminase mRNA or inhibitors of stabilization of the glutaminase mRNA as well as compounds which increase degradation of the glutaminase mRNA. For example, as shown in FIG. 2, nerve growth factor (NGF) is produced by keratinocytes in response to inflammation and is taken up and retrogradely transported to the neuronal cell body where it stimulates increased production of GT. In addition, increased production of GT also occurs from stabilization of GT mRNA via zeta-crystallin:quinone oxidoreductase (ZC) (FIG. 2). Therefore, a compound capable of neutralizing or inhibiting ZC or NGF also falls within the scope of the terms "glutaminase inhibitor" or "GT inhibitor". One specific example of a compound functioning in this manner is dicoumarol (DC), which is shown herein to inhibit ZC activity and thus inhibit GT production, thereby relieving pain. Therefore, the terms "glutaminase inhibitor", "inhibitor of glutaminase enzyme activity" and "inhibitor of glutaminase synthesis" can all be used interchangeably herein.

The method of alleviating chronic pain of the present invention results in pain relief (both thermal and mechanical) for several days by way of peripheral glutaminase inhibition without any resulting acute pain behavior, as observed by the prior art methods, such as application of capsaicin cream. While the initial experiments described herein have utilized injection of an inhibitor of neurotransmitter synthesis, the inhibitor of neurotransmitter synthesis should also be amenable to topical or oral application. For example, an oral glutaminase inhibitor given as a prodrug or with limited to substantially no penetration into the central nervous system would also be effective in producing widespread pain relief. Therefore, it is to be understood that the method of alleviating chronic pain of the present invention is not limited to injection of an inhibitor of neurotransmitter synthesis but also includes other methods of application of such inhibitor(s), such as, but not limited to, oral, topical, transdermal, parenteral, subcutaneous, intranasal, intramuscular and intravenous routes, including both local and systemic applications. In addition, the formulations containing at least one inhibitor of neurotransmitter synthesis described herein may be designed to provide delayed or controlled release using formulation techniques which are well known in the art. Using such methods of delayed or controlled release would provide an even longer period of pain relief.

The term "subject" as used herein will be understood to include a mammal, that is, a member of the Mammalia class of higher vertebrates. The term "mammal" as used herein includes, but is not limited to, a human.

The term "method of alleviating pain" as used herein will be understood to include a reduction, substantial elimination or substantial amelioration of the condition of pain, including nociceptive behavior in response to mechanical or thermal stimuli. The term "nociceptive responses" as used herein will be understood to refer to responses that occur in reaction to pain, such as mechanical or thermal stimuli.

The term "pain" as used herein will be understood to refer to all types of pain, including acute pain and chronic pain. The term "chronic pain" as used herein will be understood to include, but is not limited to, pain associated with rheumatoid arthritis or osteoarthritis, neuropathic pain, pain associated with muscle damage, myofascial pain, chronic lower back pain, pain resulting from burns, and the like.

The present invention also includes a method of alleviating both acute and chronic pain in a subject for an extended period of time. The method includes administration of a combination therapy of an effective amount of at least one compound having analgesic effects that provides substantially immediate relief of acute pain in combination with an effective amount of at least one inhibitor of neurotransmitter synthesis to a subject suffering from acute and chronic pain at a site of inflammation. Such combination therapy will provide relief of both acute and chronic pain and results in a substantially immediate reduction of nociceptive responses at the site of inflammation that last for a period of at least two days without any resulting acute behavior. Compounds having analgesic effects that may be utilized in such a method are known to those of ordinary skill in the art and include, but are not limited to, benzocaine, lidocaine, novocaine, and the like. In addition, compounds which function as glutamate inhibitors or inhibitors of glutamate binding to glutamate receptors on peripheral sensory nerves may also be utilized as the compound having analgesic effects in the above-described combination therapy. Other compounds having analgesic effects that may be utilized in the method of the present invention include aspirin, acetaminophen, paracetamol, indomethacin, cholinergic analgesics, adrenergic agents, nonsteroidal anti-inflammatory drugs, and other like compounds known in the art. Compounds having analgesic effects are widely known, and it is well within the skill of a person having ordinary skill in the art to determine an effective amount of the compound having analgesic effects that will result in a reduction of acute pain upon administration to a subject.

Several animal models of tonic pain, eg. subcutaneous and intraarticular injections of inflammatory agents such as complete Freund's adjuvant (CFA), are used to mimic human chronic pain. During the acute phase of inflammation, bradykinin, serotonin, prostaglandins, ATP, $H^+$ and glutamate activate and/or sensitize the afferent limb of primary sensory neurons by increasing spontaneous activity, lowering activation threshold, and increasing or prolonging firing to stimuli [Benton et al, 2000; Millan, 1999; Wood and Docherty, 1997; Zhou et al, 1996]. Sensory neurons respond chronically to inflammation by increasing tachykinin (substance P [SP]) and calcitonin gene-related peptide (CGRP) expression and content in dorsal root ganglia (DRG) [Calza et al, 1998; Donaldson et al, 1992; Garrett et al, 1995; Hanesch et al, 1993; Hanesch et al, 1995; Noguchi et al, 1988; Smith et al, 1992] and enhanced immunoreactivity in the spinal dorsal horn [Marlier et al, 1991], skin and joints [Ahmed et al, 1995; Nahin and Byers, 1994]. These peptide-containing neurons also are glutamatergic [Battaglia and Rustioni, 1988; De Biasi and Rustioni, 1988; Miller et al., 1993; Miller et al., 2002], using glutaminase (GT) as the synthetic enzyme for neurotransmitter glutamate production. Despite data regarding functional, morphological, and neuropeptide alterations in sensory neurons, little is known about long-term regulation of glutamate production in tonic pain models.

Acutely, glutamate is released from central primary afferent terminals following noxious stimulation [Skilling et al., 1988; Sorkin et al., 1992; Yang et al., 1996]. Acute glutamate release in the spinal cord, along with SP and CGRP, is responsible for sensitization of spinal neurons leading to persistent or chronic changes [Dickenson, 1995; Pockett, 1995; Urban et al., 1994]. After the induction of knee joint inflammation in monkeys, glutamate-immunoreactive fibers in the spinal cord increase 30% at 4 hr and nearly 40% at 8 hr [Sluka et al, 1992]. At 24 hrs, extracellular levels of spinal glutamate in rats are 150% above controls [Yang et al, 1996] indicating a possible prolonged, activity-dependent recruitment of glutamate release from central primary afferents. These studies suggest that glutamate production and release in the spinal cord are modified in pain conditions.

Alteration in glutamate production at these acute and intermediate time points most likely represents modification in flux control and/or modifications of glutamine cycle enzymes, such as GT, via second messenger pathways [Fell, 1997; Kvamme et al, 1983]. Longer-term evaluations of glutamate metabolism have not been performed in tonic pain models as have been carried out for neuropeptides in DRG neurons. Based on previous glutamate studies and evaluations of neuropeptide production, it was hypothesized that inflammation would cause DRG neurons to increase glutaminase production. Therefore, glutaminase immunoreactivity and/or enzyme activity in the rat DRG, skin and joints was examined several days after the induction of chronic arthritis.

Rats developed inflammation in the right hindpaw with redness and edema similar to previous descriptions [Besson and Guilbaud, 1988]. Nociceptive responses to normally non-nociceptive pressures (allodynia) and decreased paw withdrawal latencies to thermal stimuli (hyperalgesia) were observed in rats with CFA induced inflammation (Table 1).

TABLE I

| Mechanical and Thermal Sensitivities | | | | | |
|---|---|---|---|---|---|
| Pressure sensitivity | Control | 66.6 ± 5.2 | 65.8 ± 4.7 | 64.1 ± 5.3 | 62.9 ± 6.7 |
| (gm) | CFA | 61.6 ± 4.4 | 5.2 ± 0.5** | 4.6 ± 00.1** | 6.5 ± 0.9 |
| Thermal sensitivity | Control | 9.5 ± 0.5 | 7.5 ± 0.6 | 8.5 ± 0.7 | 9.4 ± 0.7 |
| (sec) | CFA | 10.0 ± 0.7 | 3.2 ± 0.2** | 2.9 ± 0.8** | 4.1 ± 0.9* |

Pressure sensitivities determined with von Frey hairs are expressed as gm force. Pressure and thermal control values for each day were compared with CFA values with a Student's t test.
*p < 0.01,
**p < 0.0001

Figure 3:
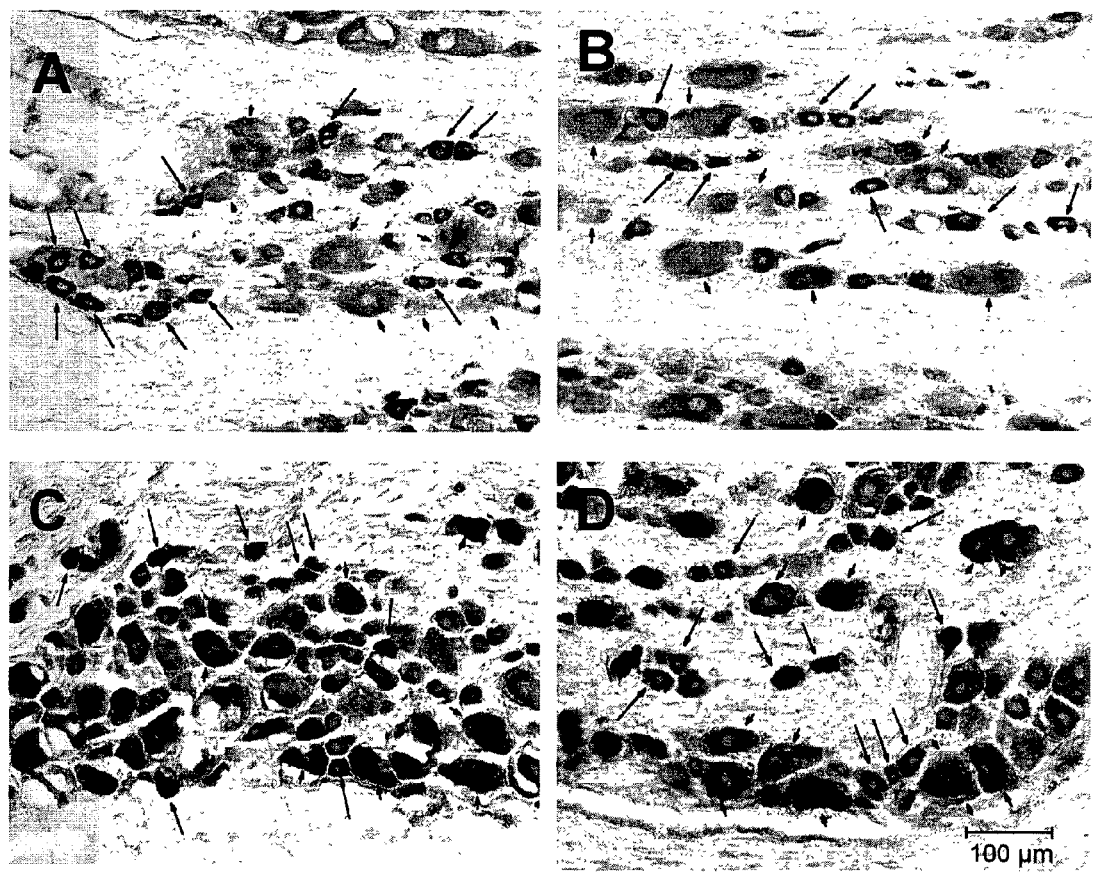
FIG. 3 are photomicrographs illustrating the effects of fixation on glutaminase (GT) immunoreactivity (IR) in the rat dorsal root ganglia (DRG). DRG sections were processed simultaneously with a mouse monoclonal GT antibody (A, C) or a rabbit polyclonal GT antiserum (B, D). Some DRG's (A,B) were fixed with 4% paraformaldehyde and others (C,D) were fixed with 70% picric acid and 0.2% paraformaldehyde. In paraformaldehyde fixed tissue, intense GT-IR was restricted to small sized DRG neurons (long arrows) with both GT antibodies (A,B). Large to medium sized neurons (short arrows) were lightly stained (A,B). In picric acid-paraformaldehyde fixed tissue, small (long arrows) and medium to large sized neurons (short arrows) contained intense GT-IR with both GT antibodies (C,D). For FIG. 4 and the data utilized to produce FIGS. 5 and 6, picric acid-paraformaldehyde fixed tissue was used with the rabbit polyclonal GT antiserum.

In normal rats, GT-IR in the DRG was evaluated with 2 fixatives and 2 antibodies. With a 4% PFA fixative, small (100–600 $\mu m^2$) neuronal cell bodies were labeled intensely with GT-IR (FIG. 3A, 3B). With the 70% PA, 0.2% PFA fixative, the majority of DRG neuronal cell bodies were labeled with both GT antibodies (FIG. 3C, 3D). The PA-PFA fixative was used for the remainder of the experiments described herein.

Figure 4:
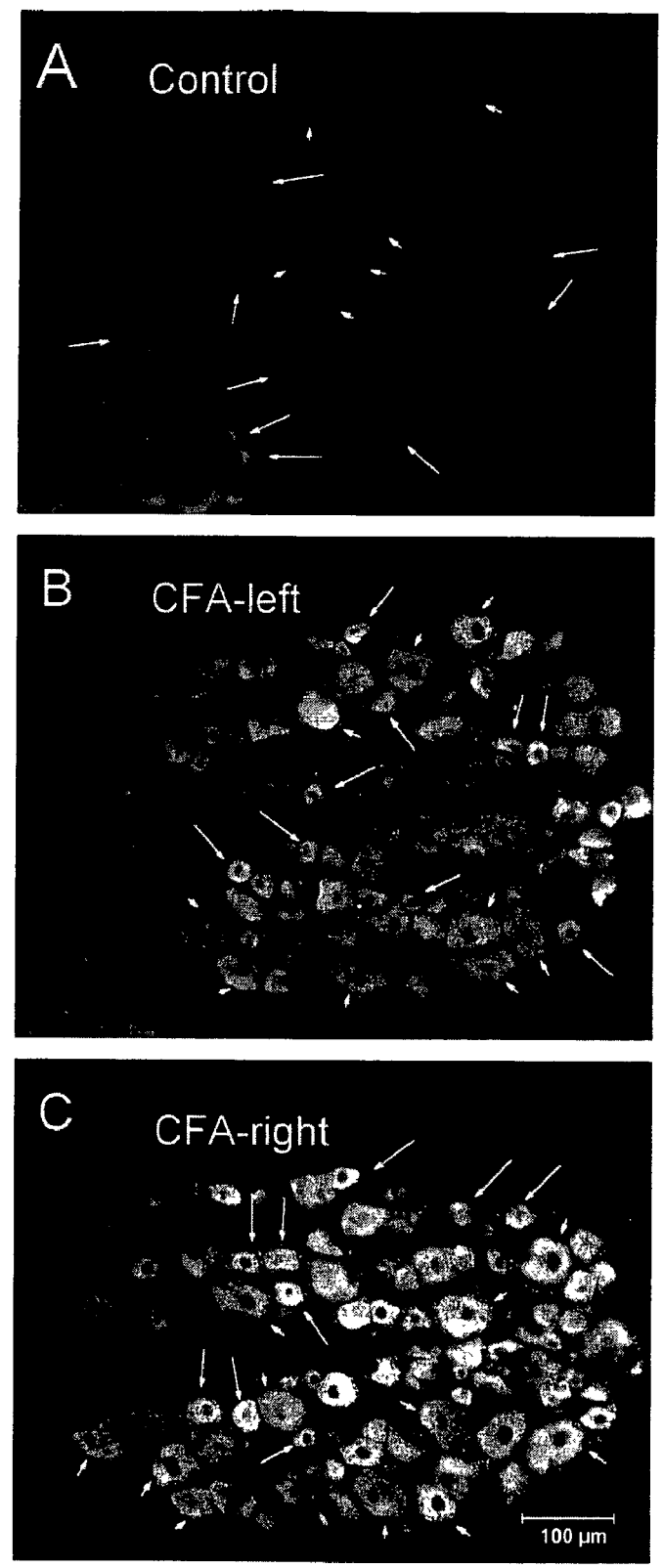
FIG. 4 are photomicrographs illustrating Glutaminase (GT) immunoreactivity (IR) in rat $L_4$ dorsal root ganglia (DRG) following 7 days of CFA inflammation in the right hindpaw. DRG sections were processed simultaneously with a rabbit polyclonal GT antiserum and photographed under identical conditions. (A) In control sections, GT-IR was light to moderate in all neuronal cell sizes, small (long arrows) and medium to large (short arrows). (B) Increased GT-IR intensity was observed in small (long arrows) and medium to large neurons (short arrows) in the left (contralateral) DRG following right hindpaw inflammation. This modest increase of GT-IR was observed in the left DRG at 3 & 10 days, also. (C) Elevated GT-IR in small (long arrows) and medium to large (short arrows) neurons occurred in the right (ipsilateral) DRG following CFA inflammation of right hindpaw. This pattern also was observed at 3 & 10 days following inflammation.

By 3 days following CFA inflammation, right DRG cell bodies from the CFA injected rats had a marked increase in GT-IR over the left DRG and control DRG cell bodies. At 7 days, CFA rats showed the same pattern of differences as the three day rats. The qualitative differences in the intensities, however, among the control, left and right DRG cell bodies were much greater (FIG. 4). Control DRG cell bodies had a light amount of GT-IR (FIG. 4A). The left DRG cell bodies from CFA rats (FIG. 4B) showed an increase in GT-IR compared to control DRG cell bodies, whereas the right DRG cell bodies contained the greatest amount of GT-IR (FIG. 4C). Similar to the three and seven day rats, the ten day CFA rats showed the same GT-IR intensity patterns among the control, left, and right DRG cell bodies.

Figure 5:
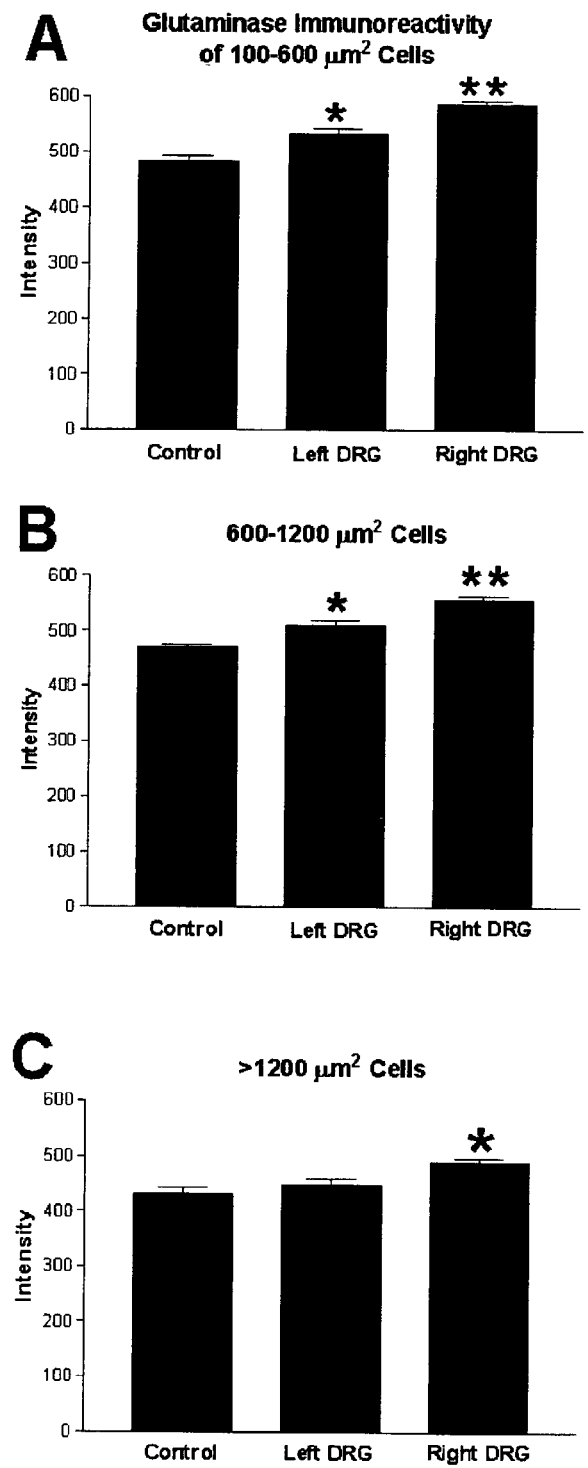
FIG. 5 is a graphic illustration of an image analysis of glutaminase (GT) immunoreactivity (IR) in $L_4$ DRG neurons after 7 days of CFA inflammation in the right paw. Data are presented as intensity divided by the area of the cell. DRG neurons were categorized into three area size groups: (A) small—100–600 $\mu m^2$, (B) medium—600–1200 $\mu m^2$, (C) large—>1200 $\mu m^2$. (A) Small sized neurons in the left DRG contained a significantly greater immunoreactive signal (*, $p<0.05$) than controls. Neurons in the right DRG were more intensely stained than left DRG or controls (**, $p<0.01$). (B) Medium sized neurons in the left DRG contained a significantly greater immunoreactive signal (*, $p<0.05$) than controls. Neurons in the right DRG were more intensely stained than left DRG or controls (**, $p<0.01$). (C) In the right DRG, large sized neurons were more intensely stained than the left DRG or controls (*, $p<0.05$).

The seven day rat immunohistochemistry images were analyzed with the SCION image analysis program in order to quantify the GT-IR intensities of three different sizes of DRG cell bodies (FIG. 5). The small (100–600 $\mu m^2$) DRG cell bodies showed the greatest amount GT-IR/area and the largest differences in intensities among control, left, and right cell bodies of the three different DRG cell sizes. The small DRG cell bodies had intensities of 484.6±2.0/$\mu m^2$ for controls, 532.6±1.7/$\mu m^2$ for the left DRG from CFA rats, and 585.6±7.7/$\mu m^2$ for the right DRG from CFA rats (FIG. 5A). The GT-IR intensities for the medium (600–1200 $\mu m^2$) DRG cell bodies were 469.3±4.9/$\mu m^2$ for the control, 509.6±8.9/$\mu m^2$ for the left DRG from CFA rats, and 556.9±7.7/$\mu m^2$ for the right DRG from CFA rats (FIG. 5B). Finally, the GT-IR intensities for the large (>1200 $\mu m^2$) DRG cell bodies were 431.6±12.2/$\mu m^2$ for the control, 448.5±10.7/$\mu m^2$ for the left DRG from CFA rats, and 491.0±5.8/$\mu m^2$ for the right DRG from CFA rats (FIG. 5C).

Figure 6:
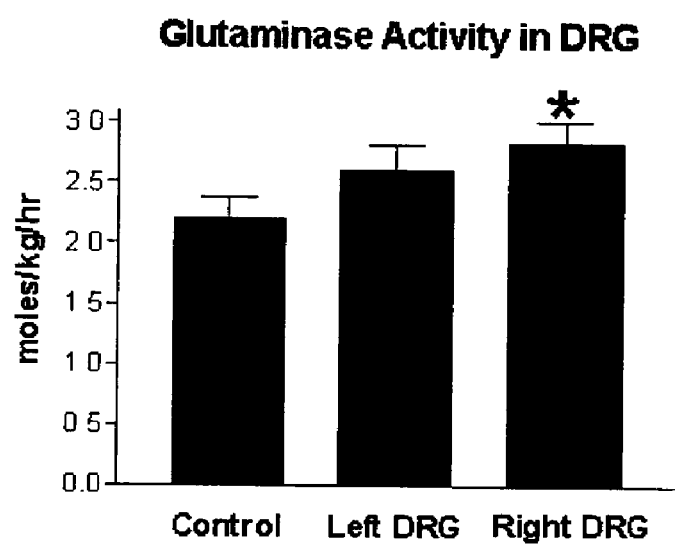
FIG. 6 is a graphic illustration of GT enzyme activity in the $L_4$ DRG at 7 days following CFA inflammation in the right hindpaw. GT activity from the right DRG ($2.83\pm0.30$ moles/kg/hr) was elevated (*, $p<0.05$) over control values ($2.20\pm0.18$ moles/kg/hr). The left (contralateral) $L_4$ DRG ($2.61\pm0.20$ moles/kg/hr) was not significantly different from controls or the right (ipsilateral) DRG.

Increased GT enzyme activity was observed in seven day CFA rats from both the left and right $L_4$ DRG's compared to control $L_4$ DRG's (FIG. 6). Control DRG's contained GT enzyme activity of 2.20±0.18 moles/kg/hr, whereas left and right DRG's from CFA rats had GT enzyme activities of 2.61±0.20 moles/kg/hr and 2.83±0.30 moles/kg/hr, respectively.

Following inflammation, alterations in intensity and distribution of glutamate and GT nerve fibers were noticeable in the skin at 3, 7, and 10 days. Control tissue had weak to moderate immunostaining for glutamate and GT (see FIG. 12A). Compared to control tissue, glutamate and GT immunoreactivity was more intense (see FIG. 12B) in the dermal nerve plexus and papillae from rats with inflammation. In addition, many glutamate and GT immunoreactive fibers were found to leave the dermis to enter the epidermis in the inflamed paw.

Once it was determined that GT levels were elevated at the neuronal cell body and peripheral fibers and in response to chronic inflammation, several GT inhibitors were examined for their ability to alleviate nociceptive responses to thermal and mechanical stimuli. Several compounds inhibit GT enzyme activity (Shapiro et al., 1978, 1979; Kvamme et al., 1975, 1991; Kvamme & Torgner, 1975; Curthoys & Watford, 1995), including 6-diazo-5-oxo-L-norleucine (DON) and N-ethylmaleimide (NEM). DON irreversibly binds to the glutamine binding site of GT (Shapiro et al., 1979), whereas NEM partially inhibits GT via interaction with the glutamate binding site (Kvamme & Olsen, 1979; Kvamme & Lenda, 1982). Intraparenchymal or ICV injection of DON inhibits GT and causes a decrease in glutamate and GT for several days in rat brain until neurons synthesize new GT (Bradford et al., 1989; Kaneko et al., 1992; Conti & Minelli, 1994). Therefore, DON and NEM were administered peripherally during chronic inflammation to observe the effect of GT enzyme inhibition on nociceptive responses.

Figure 7A:
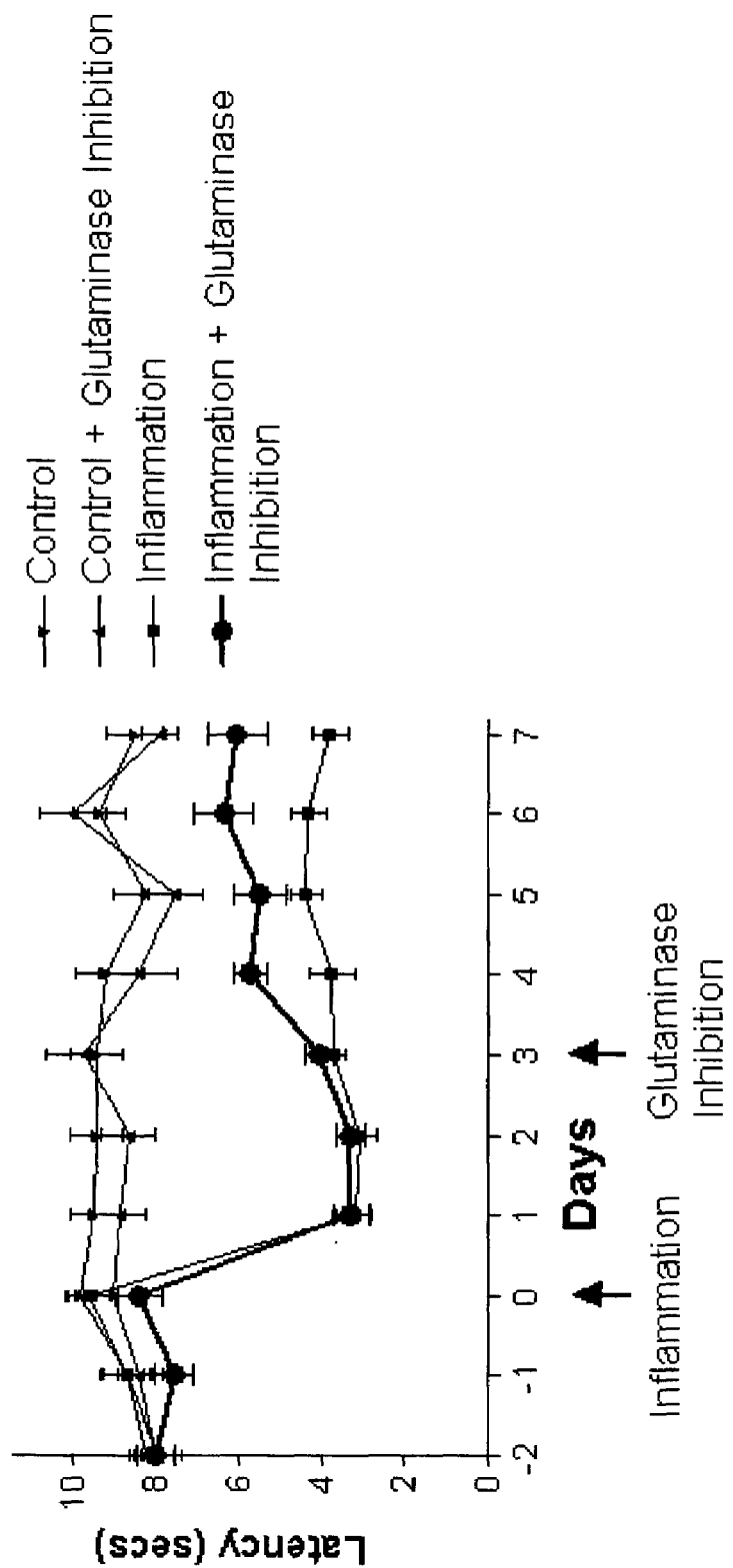
FIG. 7 is a diagrammatic representation of the effects of inhibition of glutaminase on thermal and mechanical pain. The hindpaw responses to thermal stimulation (FIG. 7A) and pressure sensitivity (FIG. 7B) were determined for a control rat, a control rat following glutaminase inhibition with 6-diazo-5-oxo-L-norleucine (DON), a rat after CFA inflammation, and a rat after CFA inflammation and following glutaminase inhibition with DON.
Figure 7B:
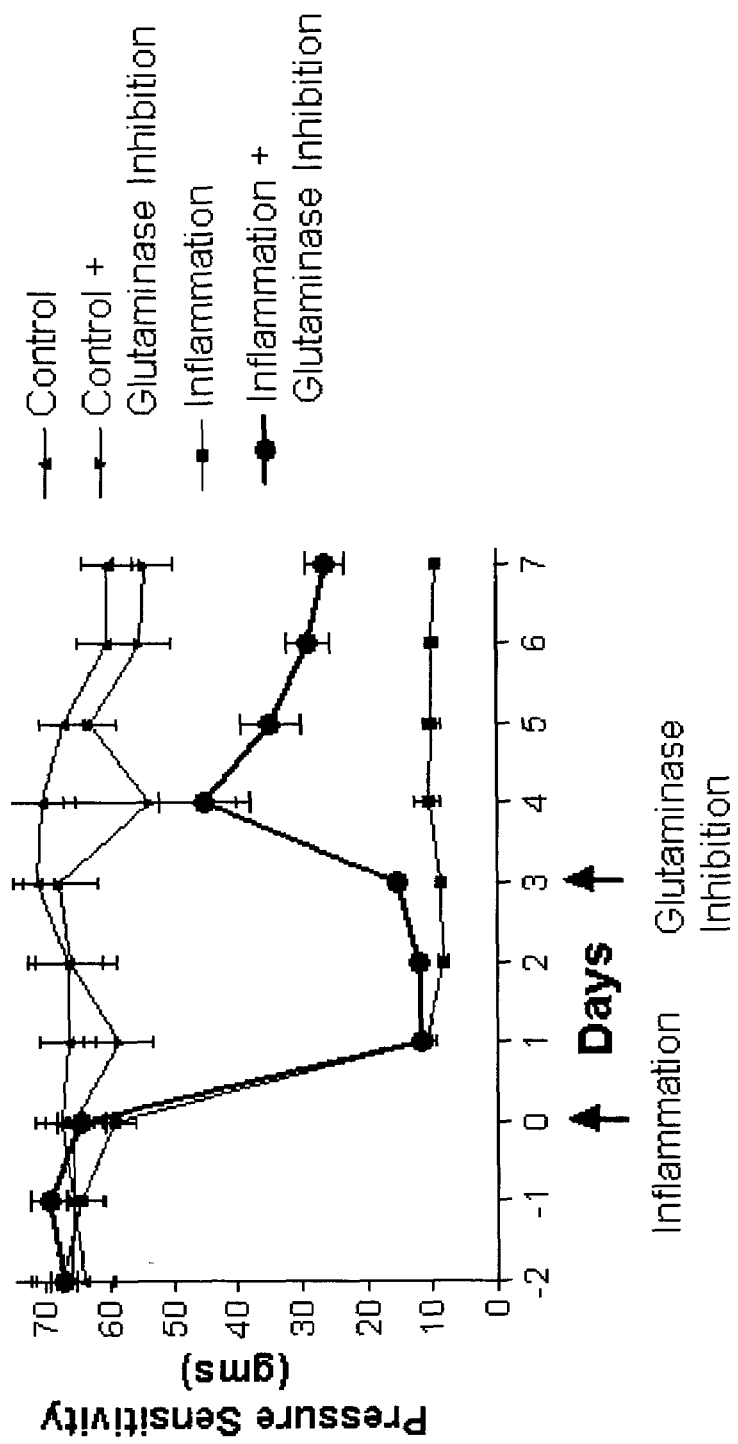

Following inflammation of the rat paw with complete Freund's adjuvant (CFA), DRG neurons increase glutaminase (GT) production for shipment to peripheral terminals causing elevated glutamate (GLU) levels in skin and joints. Increased glutamate release may be responsible for maintaining thermal hyperalgesia and/or mechanical allodynia. In the present invention, the effects of several GT inhibitors, including 6-diazo-5-oxo-L-norleucine (DON) and N-ethylmaleimide (NEM), were examined following inflammation. In FIG. 7, CFA:saline or saline was injected (75–100 μl) into the right footpad of adult male Sprague Dawley rats. After 2–3 days, DON or saline was injected (25 μl) into the right paw.

The hindpaw responses of rats to thermal stimulation and pressure sensitivity were determined in control and CFA rats, as well as control and CFA rats treated with the glutaminase inhibitor DON (FIG. 7). Paw pressure withdrawal thresholds (PPWT) were evaluated with Von Frey hairs. In rats with CFA+saline, PPWT were reduced from 50–70 g (in control rats) to 5–12 g. For CFA+DON rats, PPWT were increased to 20–30 g starting from 6 hours through the duration of the experiment. For CFA+NEM rats, PPWT were increased to 20–25 g after 48 hours.

Figure 8A:
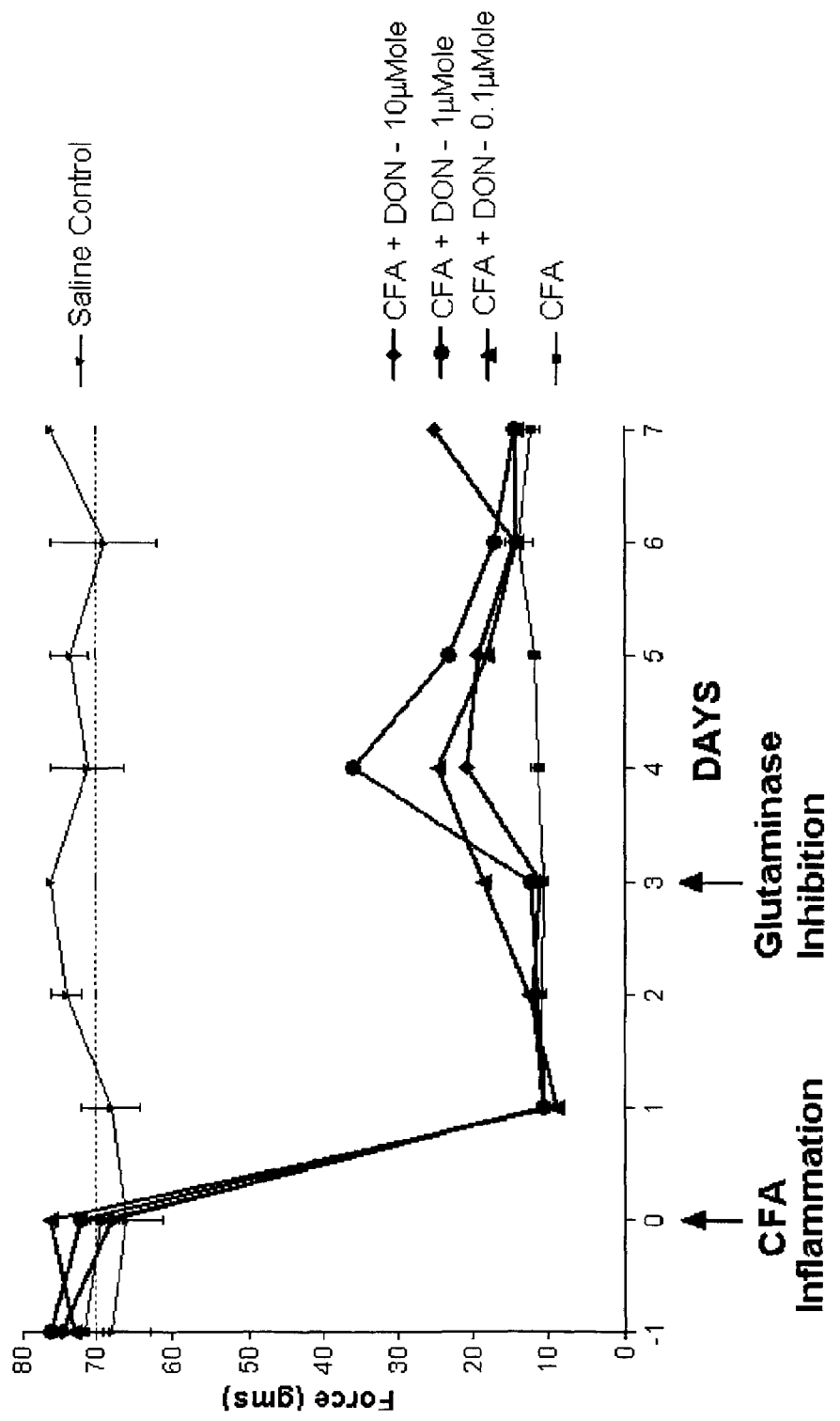
FIG. 8A is a graphic representation illustrating the efficacy of DON to provide long term pain relief from pressure (mechanical stimulation). After administration of DON at day three following CFA inflammation, pain relief occurred for several days with three different doses of DON (0.1–10 $\mu$Mole/25 $\mu$l).

In FIG. 8A, the efficacy of DON to provide long term pain relief to pressure (mechanical stimulation) was determined by using three different doses of DON (0.1–10 μMole/25 μl). After administration of DON at day three following CFA inflammation, pain relief occurred for several days with all three doses of DON.

Figure 8B:
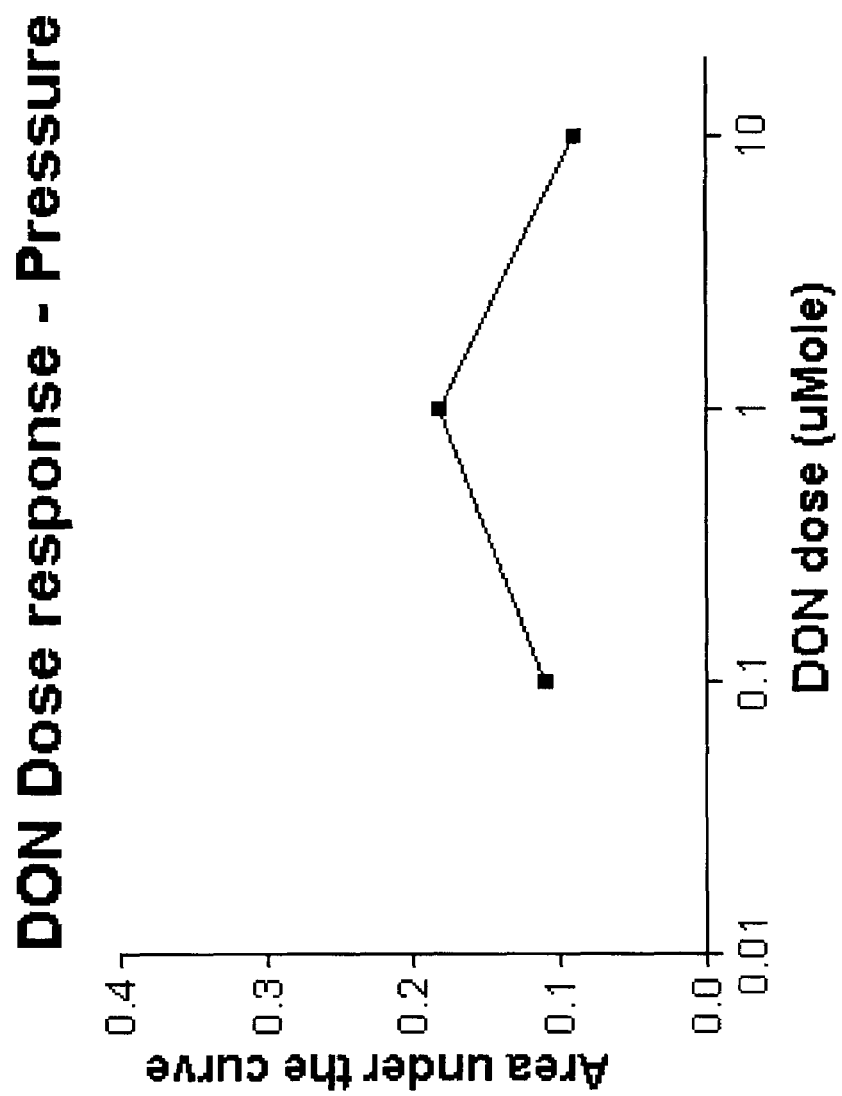
FIG. 8B is a graphic representation representing the DON dose response for pain relief from pressure stimulation. The area under the curve for each dose was determined from Day 3 to Day 5. No differences in the amount of pain relief were determined for the doses tested (0.1–10 $\mu$Mole/25 $\mu$l).

Based on the data in FIG. 8A, a dose response curve was constructed, as shown in FIG. 8B. The area under the curve for each dose was determined from Day 3 to Day 5. No differences in the amount of pain relief were determined for the doses tested (0.1–10 μMole/25 μl).

Figure 9A:
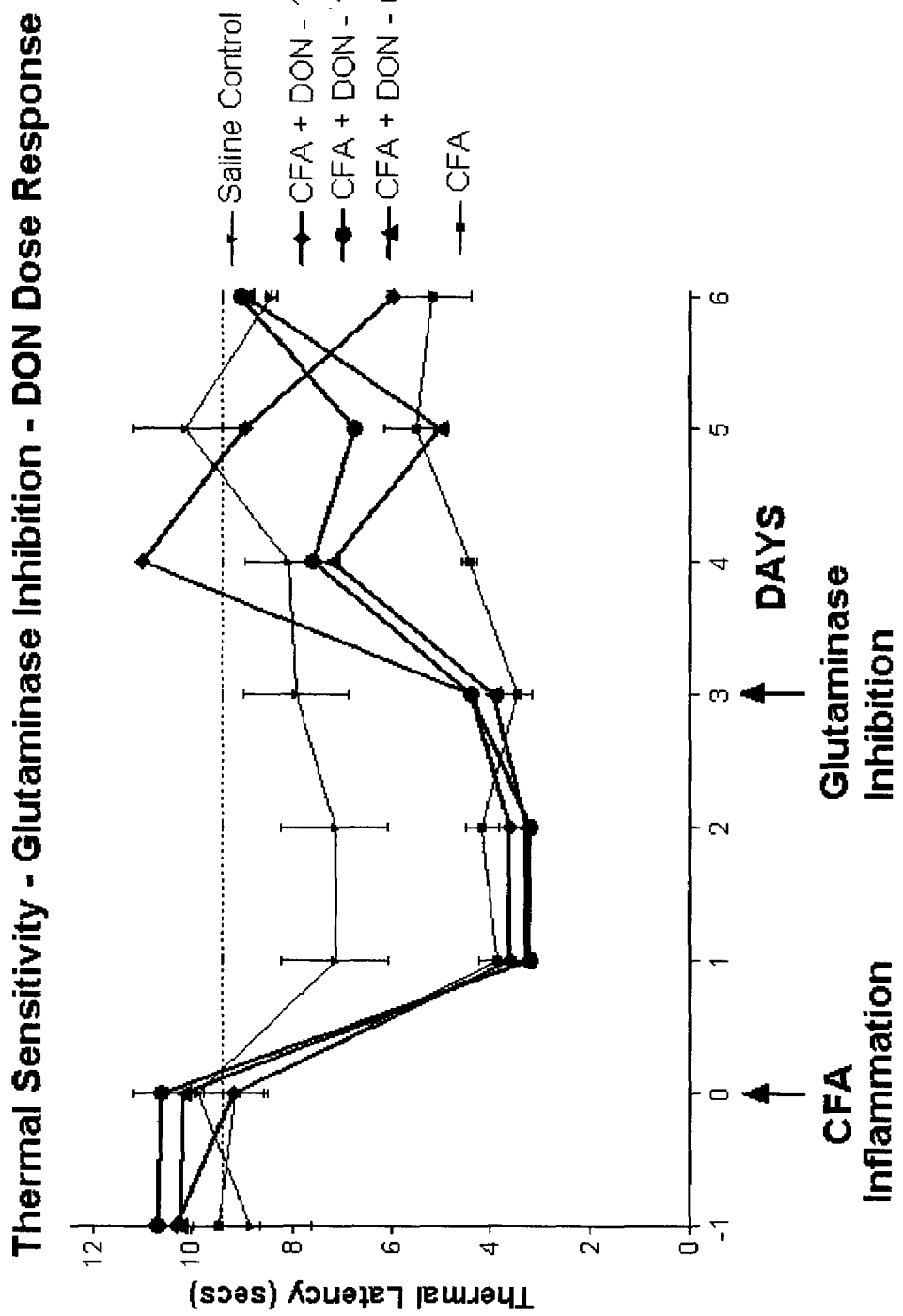
FIG. 9A is a graphic representation illustrating the efficacy of DON to provide long term pain relief to heat. After administration of DON at day three following CFA inflammation, pain relief occurred for several days with three different doses of DON (0.1–10 $\mu$Mole/25 $\mu$l).

In FIG. 9A, the efficacy of DON to provide long term pain relief to heat (thermal stimulation) was determined for the same three doses of DON (0.1–10 μMole/25 μl). After administration of DON at day 3 after CFA inflammation, pain relief occurred for several days with all three doses of DON. 10 μMole DON (♦ line) was most efficacious), bringing thermal responses back to normal for two days. The other two doses (0.1 and 1 μMole, ▲ and ● lines, respectively) provided pain relief to near normal levels for at least one day and then gave variable results for the next several days.

Figure 9B:
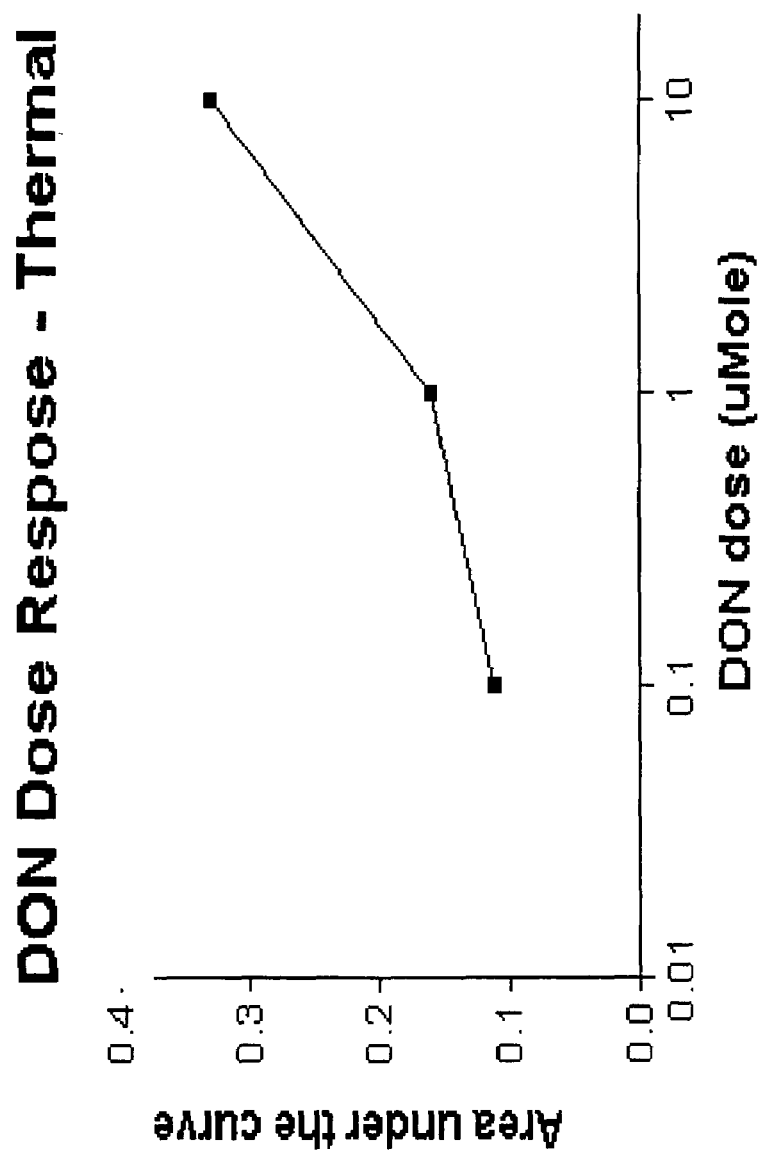
FIG. 9B is a graphic representation illustrating the DON dose response for pain relief from thermal stimulation. The area under the curve for each dose was determined from Day 3 to Day 5. Pain relief was most efficacious at the higher doses (1–10 $\mu$Mole/25 $\mu$l).

Based on the data in FIG. 9A, a dose response curve was constructed, as shown in FIG. 9B. The area under the curve for each dose was determined from Day 3 to Day 5. Pain relief was most efficacious at the higher doses (1–10 μMole/25 μl).

Figure 10A:
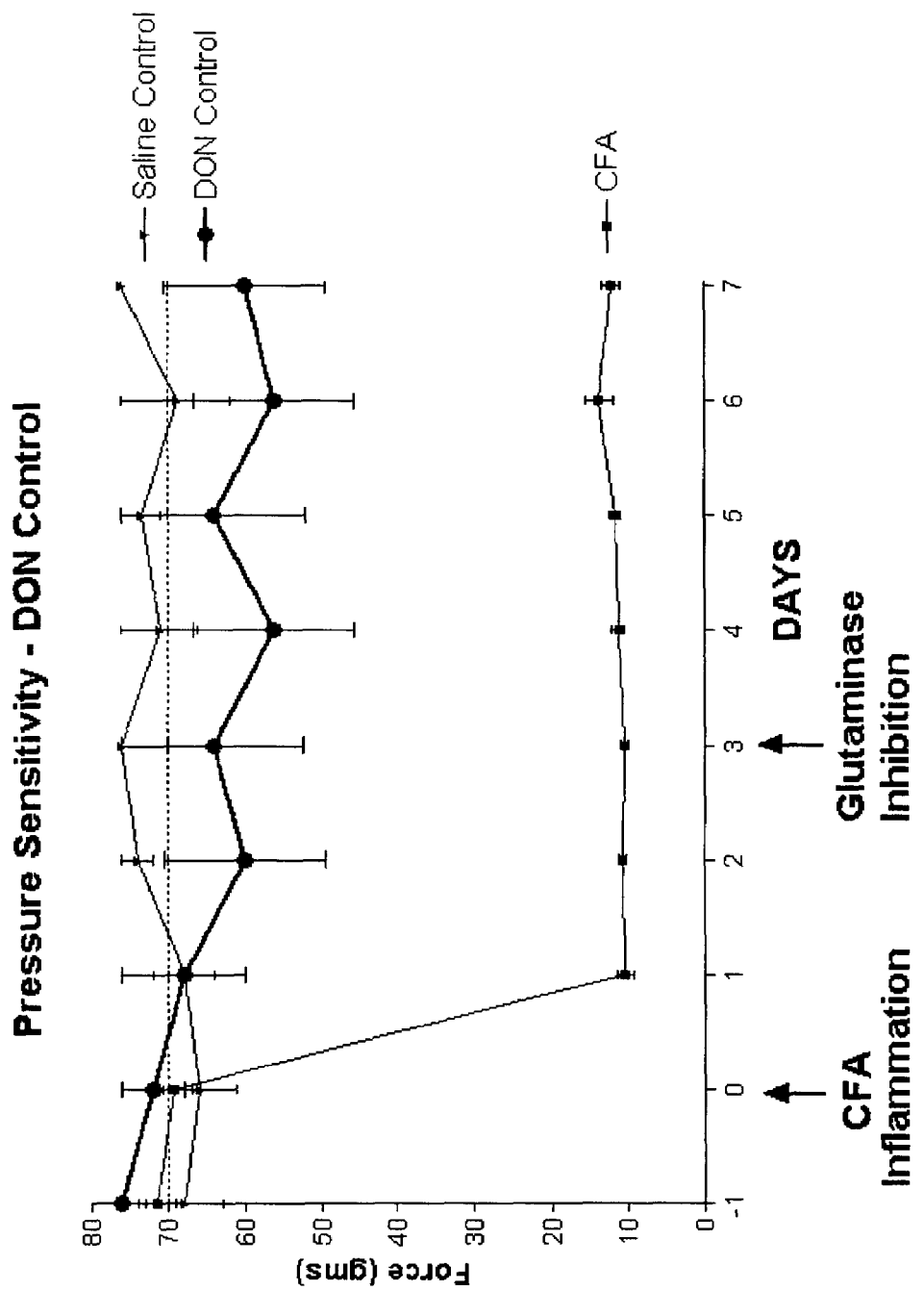
FIG. 10 are graphic representations illustrating that intraplantar injection of DON into the hindpaw of normal rats does not affect pressure or thermal senstivities. DON was injected (10 $\mu$Mole/25 $\mu$l) on day three. Both the pressure (FIG. 10A) and thermal (FIG. 10B) sensitivities in DON-treated rats were the same as saline controls.
Figure 10B:
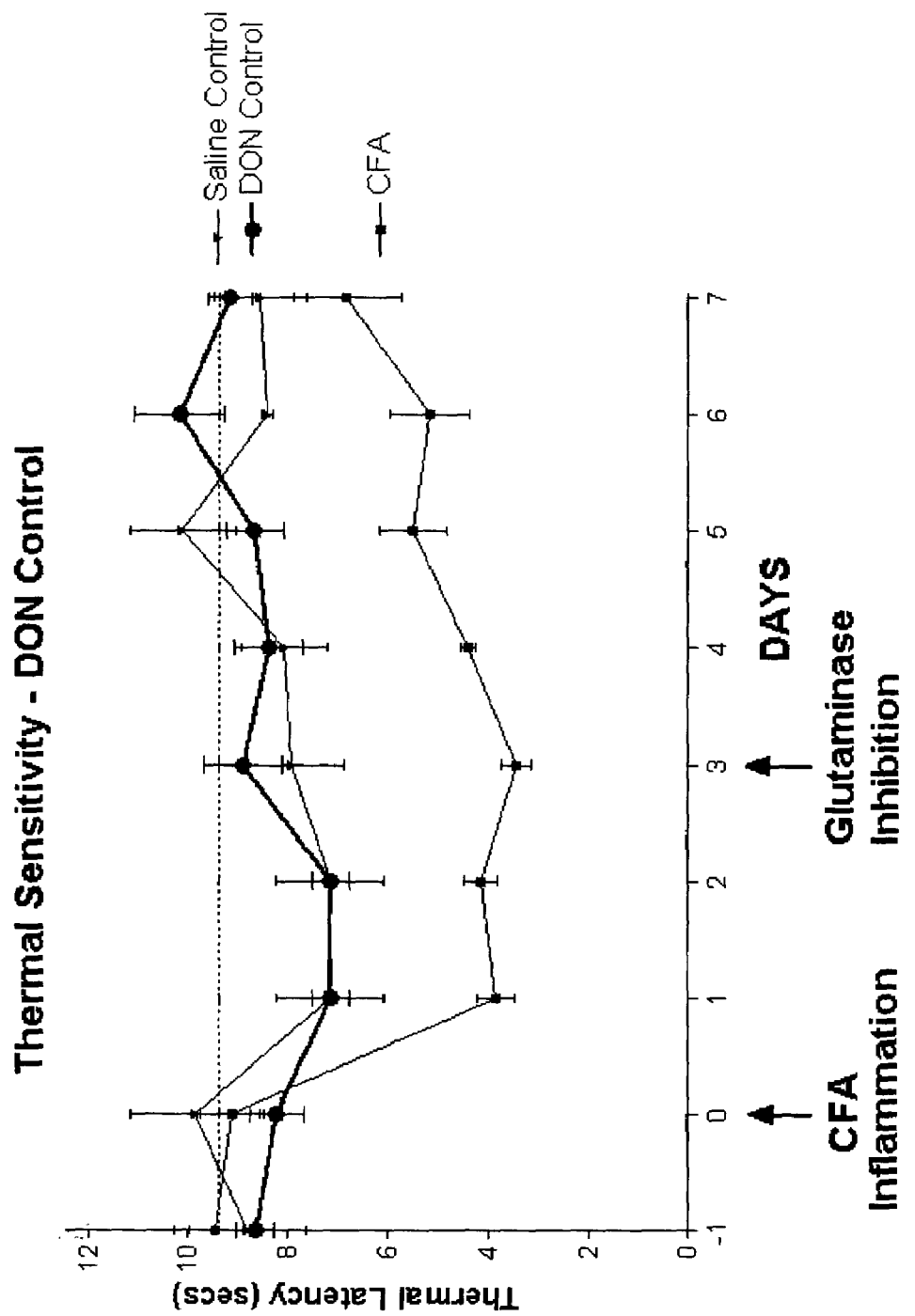

FIG. 10 illustrates DON controls. DON was injected (10 μMole/25 μl) on day 3, and such injection of DON does not affect thermal or pressure sensitivities. Both the pressure (FIG. 10A) and thermal (FIG. 10B) sensitivities in DON treated rats were the same as saline controls.

Figure 11A:
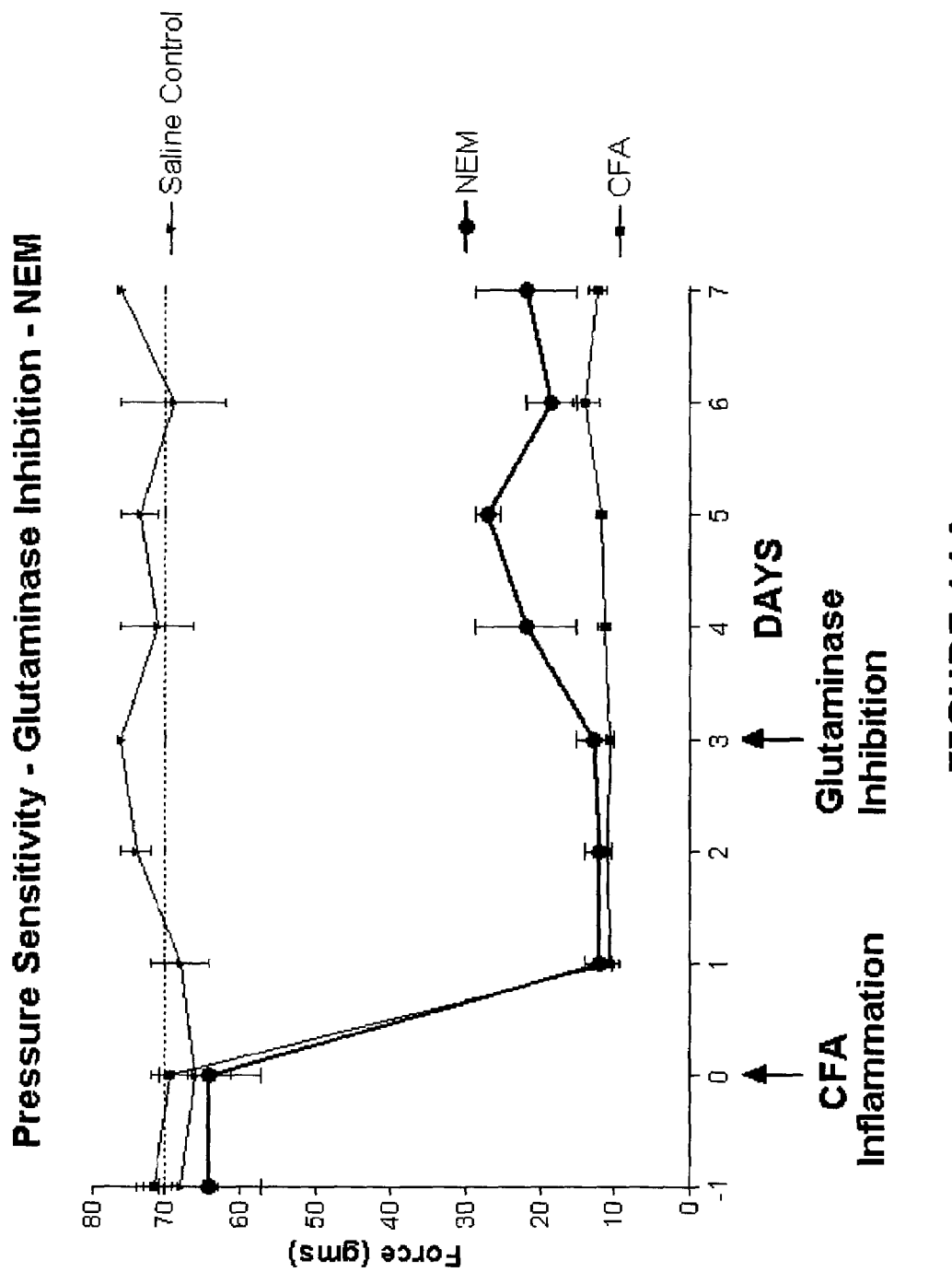
FIG. 11A is a graphic representation demonstrating the efficacy of N-ethylmaleimide (NEM) to provide long term pain relief to pressure (mechanical stimulation). After administration of NEM (10 mM/25 $\mu$l) at day three following CFA inflammation, pain relief occurred for several days.
Figure 11B:
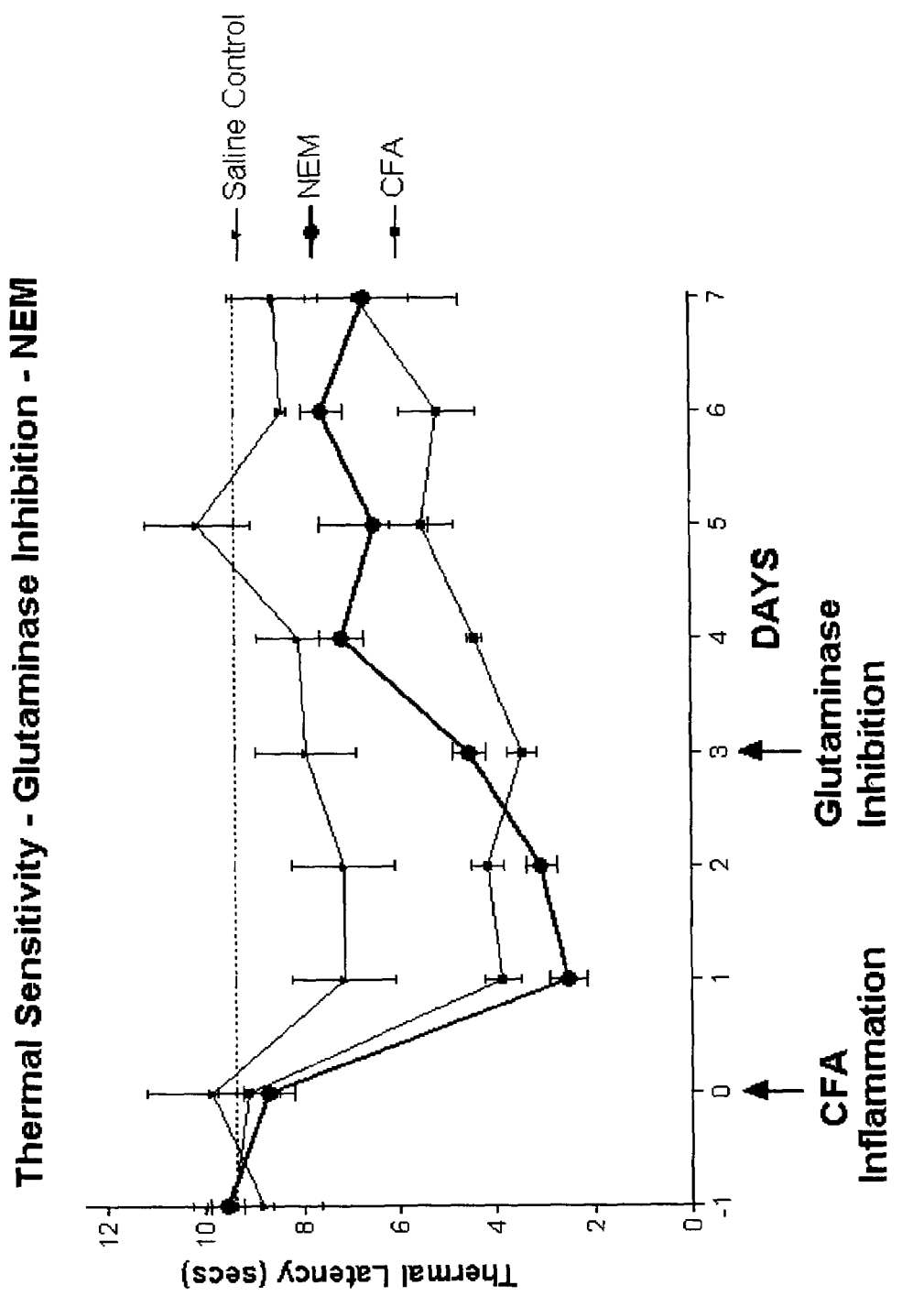
FIG. 11B is a graphic representation illustrating the efficacy of NEM to provide long term pain relief from heat. After administration of NEM (10 mM/25 $\mu$l) at day three following CFA inflammation, pain relief occurred to near normal levels at days 4 and 6.

A second GT inhibitor, N-ethylmaleimide (NEM), was also evaluated to determine its effects on GT enzyme inhibition and nociceptive response in the chronic inflammation model described above. NEM is a GT inhibitor that binds to the glutamate site of the enzyme. FIG. 11 illustrates that NEM is effective in providing long term pain relief to pressure (mechanical stimulation, as shown in FIG. 11A) and heat (thermal stimulation, as shown in FIG. 11B). After administration of NEM (10 mM/25 µl) at day three following CFA inflammation, pain relief occurred for several days in response to mechanical stimulation (FIG. 11A), while pain relief occurred to near normal levels at days four and six for thermal stimulation (FIG. 11B).

Figure 12:
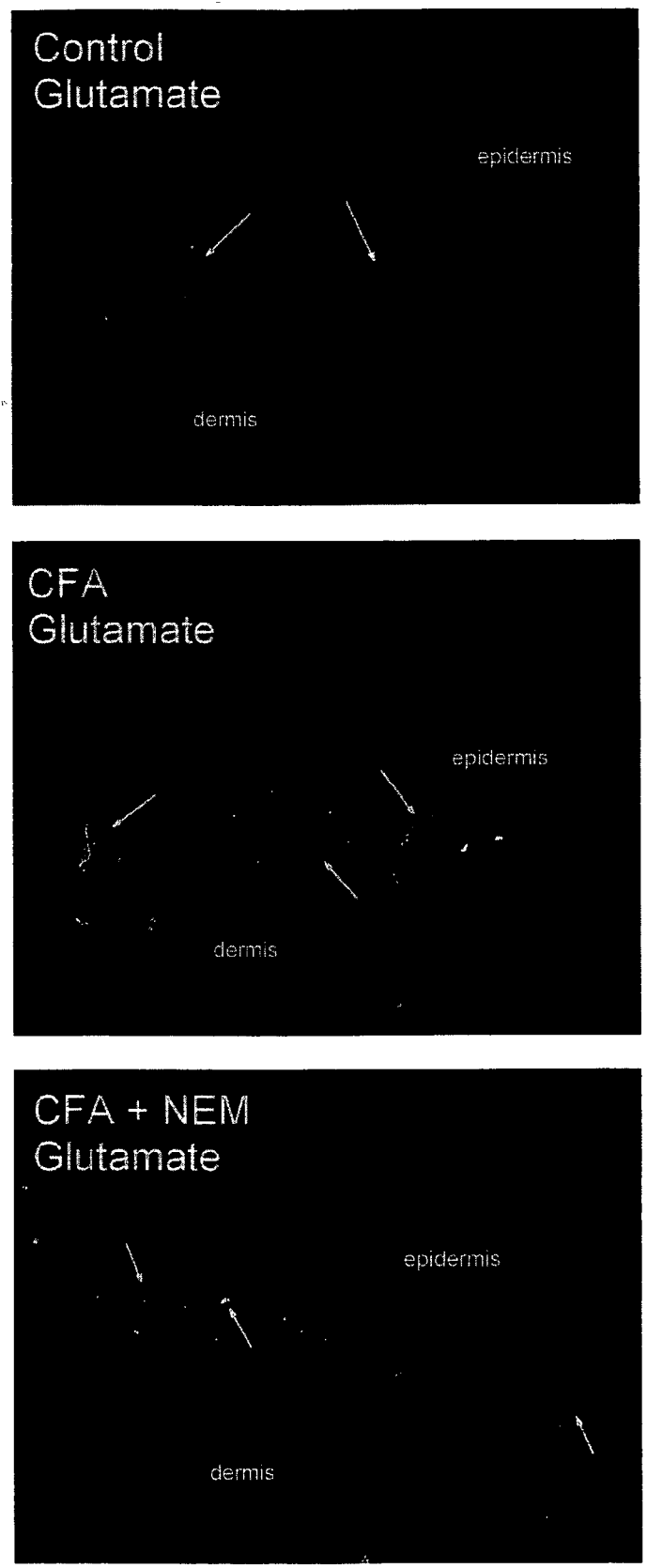
FIG. 12 are photomicrographs illustrating glutamate immunoreactivity in tissue sections from the hindpaw skin of a control rat (FIG. 12A), a rat after CFA inflammation (FIG. 12B), and a rat after CFA inflammation and following glutaminase inhibition with NEM (FIG. 12C).

The skin from the hindpaws were also processed for GLU and GT immunohistochemistry after 7 days (FIG. 12). Control rats had very little GLU- or GT-immunoreactive (IR) fibers in the paw skin. Skin from CFA+saline rats contained many intense GLU-IR and GT-IR fibers. Skin from CFA+DON or CFA+NEM rats had moderate numbers of GLU-IR and GT-IR fibers.

Figure 13A:
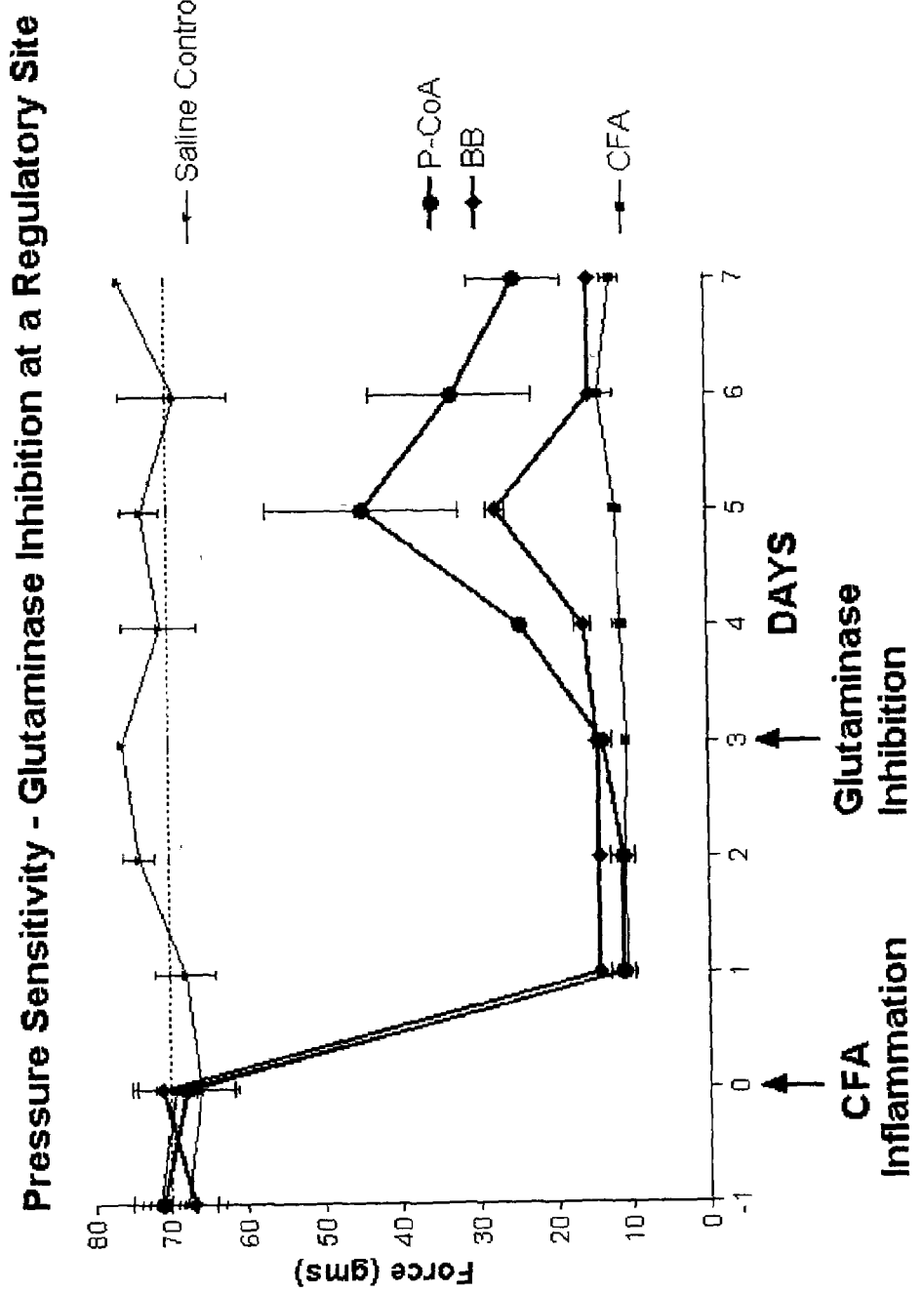
FIG. 13A is a graphic representation demonstrating the use of two inhibitors at regulatory sites on glutaminase and their efficacy to provide long term pain relief to pressure (mechanical stimulation). After administration of Palmitoyl Coenzyme A (P-CoA, 2 mM/25 $\mu$l) or bromothymol blue (BB, 200 $\mu$M/25 $\mu$l) at day three following CFA inflammation, pain relief occurred for several days.
Figure 13B:
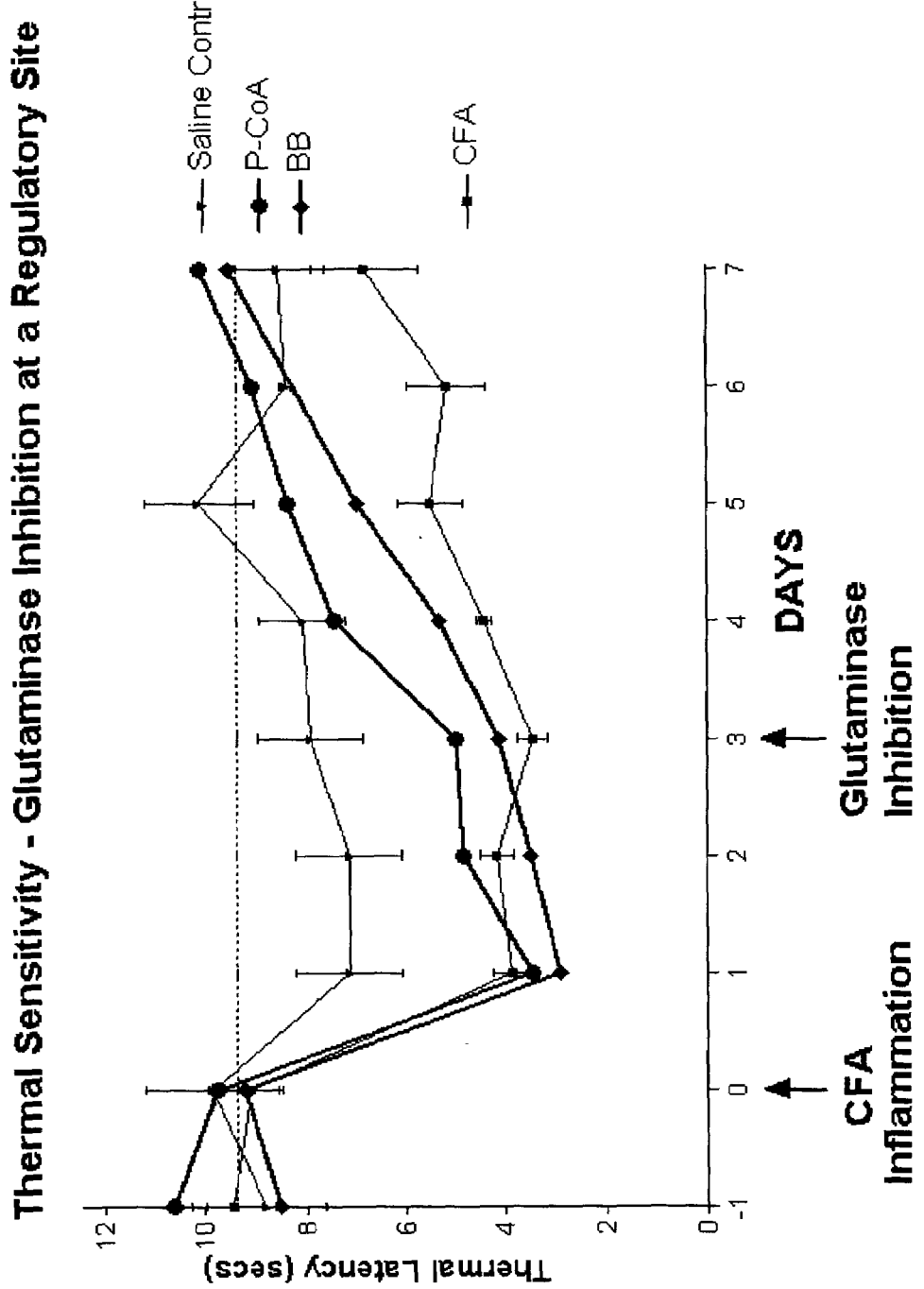
FIG. 13B is a graphic representation illustrating the efficacy of P-CoA and BB to give long term pain relief to heat. After administration of P-CoA (2 mM/25 $\mu$l) at day three following CFA inflammation, pain relief occurred to near normal levels from Days 4–7. After BB (200 $\mu$M/25 $\mu$l), pain relief occurred from Days 5–7 and at near normal levels from Days 6–7.

Two other GT inhibitors, BB and P-CoA, were also evaluated to determine their effects on GT enzyme inhibition and nociceptive responses in the chronic inflammation model described above. P-CoA and BB are inhibitors of GT at regulatory sites on the enzyme. P-CoA (2 mM/25 µl) or BB (200 µM/25 µl) was administered at day three following CFA inflammation, and both were shown to be effective in providing long term pain relief to pressure (mechanical stimulation, as shown in FIG. 13A) and heat (thermal stimulation, as shown in FIG. 13B). In FIG. 13A, P-CoA (● line) provided pain relief from Days 4–7, whereas BB (♦ line) gave pain relief on Day 5. In FIG. 13B, P-CoA provided pain relief to near normal levels from Days 4–7, while BB provided pain relief from Days 5–7 and at near normal levels from Days 6 and 7.

Figure 14:
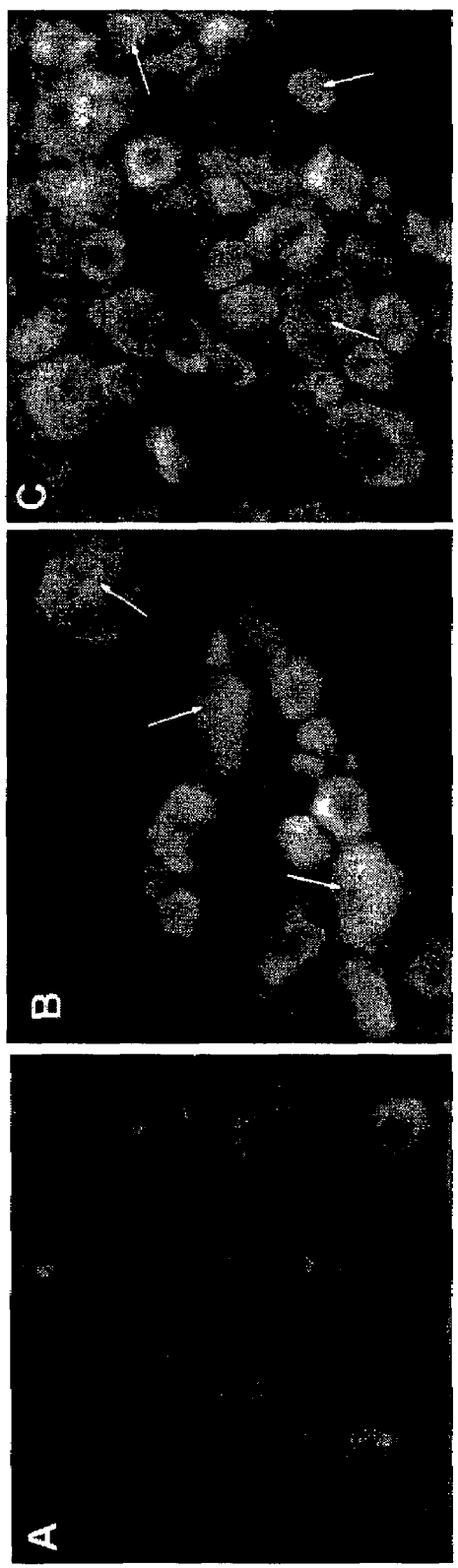
FIG. 14 are photomicrographs illustrating that glutaminase production in many cells is regulated by zeta-crystallin: quinone oxidoreductase (ZC).

FIG. 14 illustrates that glutaminase production in many cells is regulated by zeta-crystallin:quinone oxidoreductase (ZC). In FIGS. 14A–C, ZC levels are modified during chronic inflammation. ZC-immunoreactivity (IR) was examined in the rat $L_4$ DRG during inflammation at an early and later time point (2, 6 days). ZC-IR in DRG neurons of control rats (A) shows a moderate staining of the cytoplasm of all neurons. Following inflammation for 48 hrs, ZC-IR is elevated in the cytoplasm and now appears in the nuclei of many neurons (arrows). ZC-IR remains elevated at 6 days of inflammation and occurs mainly in the cytoplasm, although some nuclei (arrows) contain light ZC-IR. The increase in ZC precedes elevated amounts of glutaminase in DRG neurons during inflammation. These results are consistent with ZC's role as a stabilizer of glutaminase mRNA during times of cellular stress. Increased production of ZC during inflammation appears important for stabilization of glutaminase mRNA and elevated glutaminase production.

Figure 15:
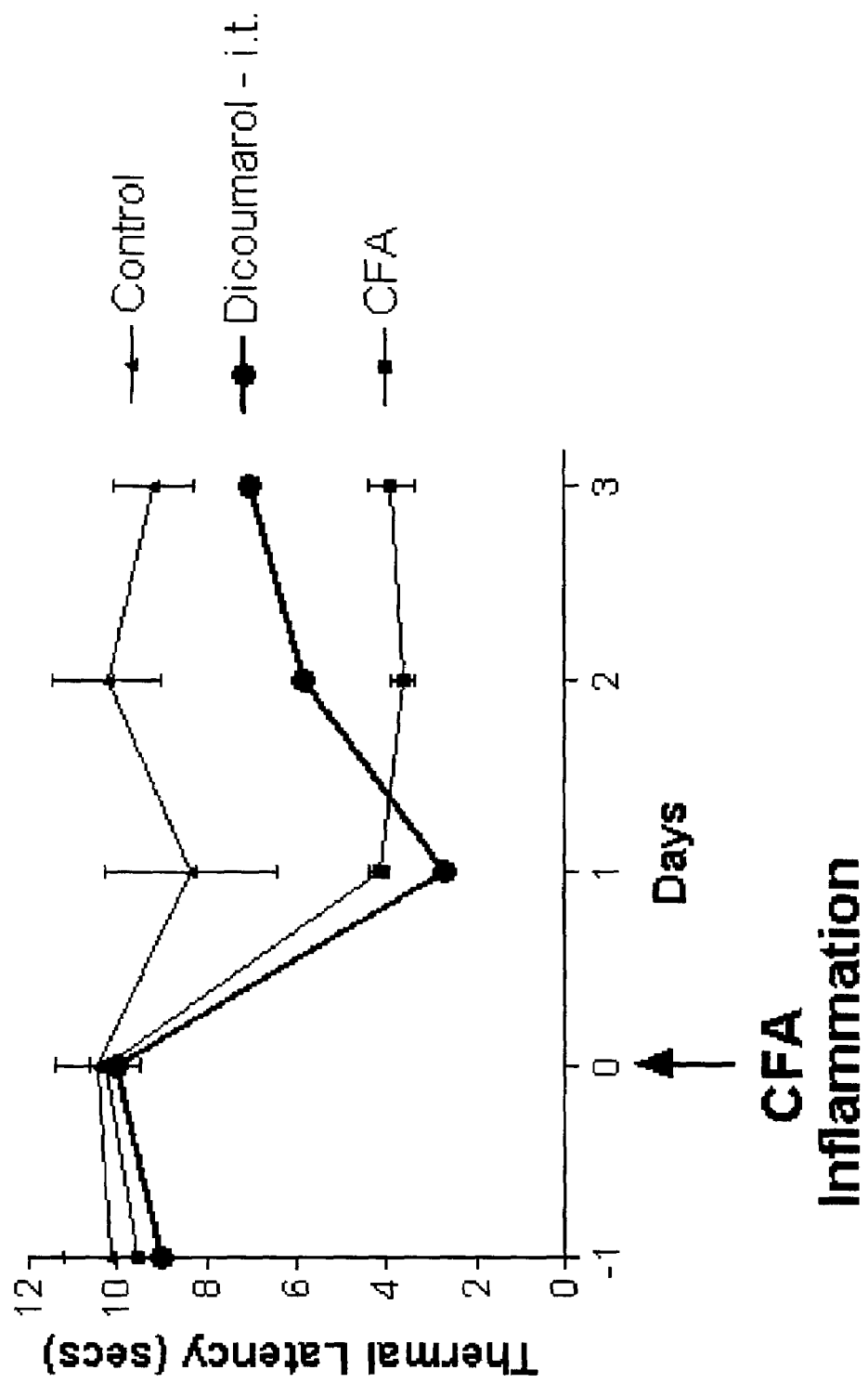
FIG. 15 is a diagrammatic representation that illustrates that dicoumarol, a ZC inhibitor, disrupts increased glutaminase production during chronic inflammation and decreases the prolonged hyperalgesia of chronic inflammation. Inflammation was initiated with complete Freund's adjuvant (CFA) at Day 0, and dicoumarol (15 µl @ 500 µM) or saline was administered intrathecally on days 0, 1 and 2. Thermal latencies and pressure responses (not shown) were recorded, and both the groups with inflammation (CFA) and inflammation plus dicoumarol (CFA+DC) experienced hyperalgesia and allodynia during acute inflammation (Day 1). As inflammation progressed, however, the responses of CFA+DC rats became less hyperalgesic and allodynic. At Day 3, the DRG's from the rats were collected and processed for glutaminase and ZC-IR, as shown in FIG. 16.
Figure 16:
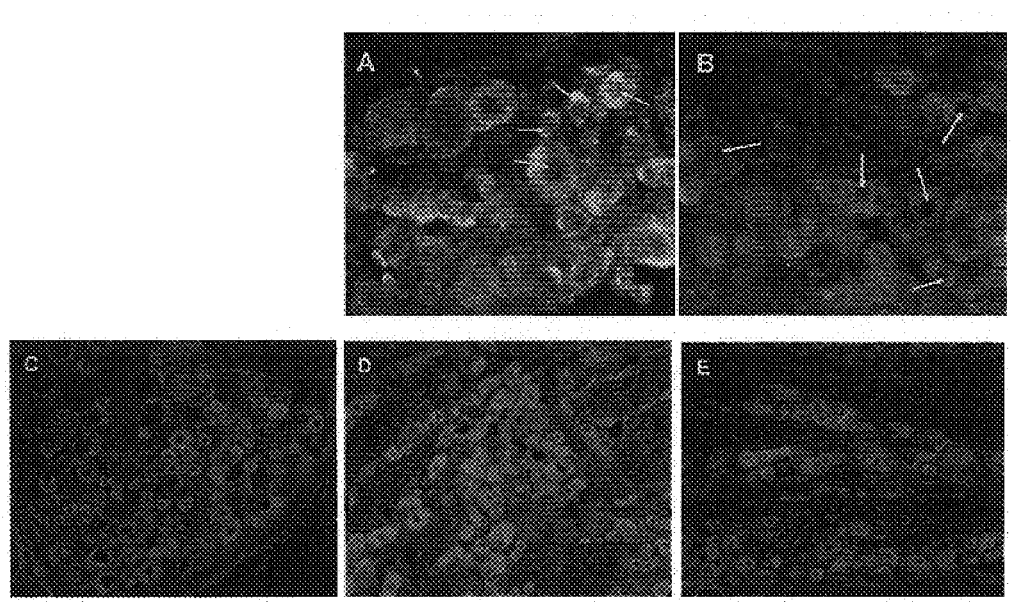
FIG. 16 are photomicrographs illustrating that dicoumarol inhibits ZC and glutaminase production. In the DRG, ZC-IR was elevated (A) in rats with inflammation, but the ZC-IR (B) from rats treated with DC during inflammation was similar to controls. ZC-IR was found in the cytoplasm and nuclei (arrows) from rats with inflammation, whereas in rats treated with DC during inflammation, the nuclei (arrows) were not stained and ZC-IR was found primarily in the cytoplasm. In the DRG, glutaminase-IR was observed at moderate levels from controls (C), elevated following inflammation (D), and similar to controls in rats treated with DC during inflammation (E).

In FIGS. 15 and 16, dicoumarol, a ZC inhibitor, is shown to disrupt increased glutaminase production during chronic inflammation and decrease the prolonged hyperalgesia of chronic inflammation. Since ZC stabilizes glutaminase mRNA, then inhibition of ZC should not allow neurons to increase glutaminase production during inflammation. Intrathecal (i.t.) cannulae were implanted to the L4 DRG, and rats recovered several days. Inflammation was initiated with complete Freund's adjuvant (CFA) at Day 0 and dicoumarol (15 µl @ 500 µM) or saline was administered i.t. on days 0, 1 and 2. Thermal latencies (FIG. 15) and pressure responses (not shown) were recorded. Both the groups with inflammation (CFA) and inflammation plus dicoumarol (CFA+DC) experienced hyperalgesia and allodynia during acute inflammation (Day 1). As inflammation progressed, however, the responses of CFA+DC rats became less hyperalgesic and allodynic. At Day 3, the DRG's from the rats were. collected and processed for glutaminase and ZC-IR (FIG. 16). In the DRG, ZC-IR was elevated (FIG. 16A) in rats with inflammation, but the ZC-IR (FIG. 16B) from rats treated with DC during inflammation was similar to controls. ZC-IR was found in the cytoplasm and nuclei (arrows) from rats with inflammation, whereas in rats treated with DC during inflammation, the nuclei (arrows) were not stained and ZC-IR was found primarily in the cytoplasm.

In the DRG, glutaminase-IR was observed at moderate levels from controls (FIG. 16C), elevated following inflammation (FIG. 16D), and similar to controls in rats treated with DC during inflammation (FIG. 16E). These data give further support to ZC's role in altering the expression of glutaminase during inflammation and that increased glutaminase is important for maintaining increased sensitivities during inflammation. In addition, it indicates that disruption of glutaminase synthesis during inflammation is potential target for providing pain relief.

Chronic Alterations in the DRG Neuronal Cell Body.

The DRG contains high levels of GT enzyme activity [Duce and Keen, 1983; Graham and Aprison, 1969; McDougal et al., 1981], but localization of GT to specific neuronal cell types has been controversial to those of ordinary skill in the art. Incubation of rat DRG's in [$^3$H]glutamine (converted to [$^3$H]glutamate via GT) labels neurons of all cell sizes [Duce and Keen, 1983]. Small sized neurons are stained exclusively with rabbit polyclonal GT antisera in PFA fixed tissue [Battaglia and Rustioni, 1988; Cangro et al, 1984, 1985], whereas most DRG neurons are stained using a mouse monoclonal GT antibody in PA-PFA fixed tissue [Miller et al, 1992, 2002]. Therefore, GT immunostaining was compared with the 2 different fixatives and antibodies. In side by side comparisons, the same pattern of GT immunostaining occurred for both GT antibodies depending on the fixative used. With PFA fixative, small sized DRG neurons were GT immunoreactive, but with PA-PFA fixative, the majority of the DRG neurons had GT-IR. This pattern is more consistent with glutamate immunohistochemistry where most DRG neurons are immunoreactive [Battagli and Rustioni, 1988; Stoyanova et al., 1998; Wanaka et al., 1987]. These results indicate that GT is sensitive to aldehyde fixation for detection with immunohistochemistry. The results from previous studies of glutaminase immunostaining [Battaglia and Rustioni, 1988; Cangro et al, 1984, 1985], therefore, may have caused glutaminase to be overlooked or underestimated as a target for pharmacological intervention for pain.

The increases in GT in the DRG after inflammation with complete Freund's adjuvant described herein further illustrate how primary sensory neurons are altered during chronic inflammation. If inflammation continues past the acute stage, the primary sensory neuron is induced into an altered phenotype making it more responsive to stimuli or sensitization. In animal tonic pain models, sensory neurons respond chronically by modifying neuropeptide, receptor, and ion channel production [Calzà et al., 1998; Donaldson et al., 1992; Garrett et al., 1995; Gould et al., 1998; Hanesch et al., 1993, 1995; Millan, 1999; Mulder et al., 1997, 1999; Nahin and Byers, 1994; Noguchi et al., 1988; Seybold et al., 1995; Smith et al., 1992; Tate et al, 1998; Zhang et al., 1998]. Increased IR for glutamate, the product of GT enzyme activity, has been observed in nerve fibers in the spinal cord of the monkey and rat after induction of experimental arthritis [Sluka et al, 1992, 1993]. This increase, presumably from primary sensory nerve fibers in the spinal cord, occurred at 4–12 hrs, but returned to normal levels by 24 hrs [Sluka et al, 1993]. In the monkey medial articular nerve, the number of glutamate-immunoreactive, unmyelinated and thinly myelinated axons increased after inflammation by 2 hrs, peaked between 4–6 hrs, and returned to baseline by 8 hrs [Westlund et al, 1992]. These acute alterations in glutamate-IR in axons and terminals cannot be attributed to alterations in the DRG neuronal cell body, but are likely to be caused by flux control mechanisms or alteration of glutamine cycle enzymes via signal transduction pathways [Curthoys and Watford, 1995; Fell, 1997]. For example, increased synaptic activity causes an elevation of phosphate by hydrolysis of ATP and an increase of calcium from entry into the nerve terminal. GT is activated by inorganic phosphate, i.e. phosphate-activated glutaminase (PAG), and phosphate activation is sensitized by calcium [Erecinska et al., 1990; Kvamme et al., 1979; Kvamme, 1998]. Thus increased electrical activity in sensory neurons at the acute stages of inflammation could cause GT activity in axons and terminals to be augmented to produce elevated amounts of glutamate [Erecinska et al, 1990; Kvamme et al, 1979, 1983, 1998].

In neurons exposed to chronic inflammation, long term regulation of glutamate levels is unlikely to be controlled in such a manner. Since DRG neuronal cell bodies have an altered phenotype that maintains or exacerbates inflammatory sensitization [Donnerer et al., 1992; Hanesch et al., 1993; Nahin and Byers, 1994; Ahmed et al., 1995; Garrett et al., 1995] and since most DRG neurons are glutamatergic [Miller et al., 1993, 2002a], it was necessary to determine if long-term alterations occur in glutamate metabolism of primary sensory neurons in chronic inflammation. Indeed, it has been shown herein that long-term elevated GT levels occur in DRG neurons during chronic inflammation. In the present invention, the largest long term increase of GT IR occurred in small and medium sized DRG neuronal cell bodies. Neurons of these sizes commonly are considered to include nociceptive neurons that give rise to unmyelinated C and lightly myelinated A-delta fibers [Cameron et al., 1986; Garry et al., 1989; Harper and Lawson, 1985; Willis and Coggeshall, 1991]. Elevated amounts of GT are likely to lead to increased production of glutamate in nociceptive, primary afferent nerve terminals in the spinal cord. SP and CGRP are found along with glutamate in primary afferent terminals [Merighi et al, 1991], and the co-release of glutamate and these neuropeptides generate hypersensitivity of spinal neurons [Besson et al, 1999]. Therefore, an increase in the amount of GT during chronic inflammation may lead to increased production and release of glutamate along with substance P and CGRP. Increased production and release of these substances could sustain spinal hypersensitivity maintaining a state of chronic pain.

Chronic Alterations in Peripheral Nerve Fibers.

Increased production of GT in the DRG cell bodies could affect the peripheral process, also. Glutamate release occurs from peripheral processes [Bledsoe et al., 1980; Jackson et al., 1993; Lawand et al., 2000; Weinreich and Hammerschlag, 1975], and peripheral nerve terminals in skin contain glutamate receptors [Carlton et al., 1995, 1998; Carlton and Coggeshall, 1999; Coggeshall and Carlton, 1998]. Peripheral administrations of glutamate receptor agonists sensitize peripheral afferents and produce nociceptive reflexes/hyperalgesia [Ault and Hildebrand, 1993a,b; Carlton et al., 1998; Davidson et al., 1997; Jackson et al., 1995; Lawand et al., 1997; Sang et al., 1998; Wang et al., 1997; Zhou et al., 1996]. Following inflammation, the number of glutamate receptor immunoreactive axons in peripheral sensory nerve increases [Carlton and Coggeshall, 1999]. It is likely, therefore, that the increased GT in DRG cell bodies causes alterations in glutamate metabolism in the peripheral nerve fibers of the primary sensory neuron. In previous studies from our laboratory and in the present invention, the sensory nerve fibers in the skin of CFA inflamed rats have elevated levels of GT and glutamate with a time course similar to the DRG [Miller et al., 1999; Miller et al., 2002]. Increased glutamate production and release from peripheral processes could activate terminals with glutamate receptors leading to further sensitization of primary afferents. The release of glutamate could affect not only the nerve terminal where it was released, but also surrounding axon terminals and local cells [Carlton et al., 1995, 1998; Carlton and Coggeshall, 1999; Coggeshall and Carlton, 1998; Genever et al., 1999]. A cycle, therefore, of increased glutamate production and release, elevated numbers of axons with glutamate receptors, and maintenance of sensitization of peripheral nerve terminals would further exacerbate the process of chronic pain from the periphery.

As stated above, long-term changes due to inflammation, as demonstrated in the present invention, include an increase in glutaminase in the rat DRG cell body. This increase in glutaminase will lead to elevated production and release of glutamate at both the peripheral and central processes of primary afferents. An increase in glutamate metabolism in primary sensory neurons may be partly responsible for heightened nociceptive sensitivity in tonic pain models. Prevention of increased glutaminase production or inhibition of glutaminase enzyme activity, therefore, may reduce or block some nociceptive responses in inflammatory models.

Prevention of Increased Glutaminase Production.

Several neurotrophic factors, particularly NGF, have a significant role in altering the phenotype of sensory neurons during chronic inflammation [Woolf, 1996; Raja, 1995; Reinert et al., 1998; Koltzenburg, 1999]. NGF levels increase in inflamed tissue and NGF neutralization with TrkA-IgG into the inflamed field prevents hyperalgesia [Koltzenberg et al., 1999; Nicholas et al., 1999]. NGF causes an increase in mRNA for growth-associated protein 43 and preprotachykinin A [SP] in DRG neurons, and anti-NGF prevents these increases [Malcangio et al., 1997; Reinert et al., 1998]. These DRG neurons also are glutamatergic, but the influence of NGF on glutamate metabolism in chronic inflammation has not been investigated. NGF influences GT expression in DRG neurons in utero and in oculo [McDougal et al., 1981; Miller et al., 1999], and preliminary data indicate that NGF influences GT expression in the DRG and peripheral primary afferents similar to inflammation [Miller et al, 2001]. Therefore, it is believed that by inhibiting NGF's role on modifying glutamate metabolism in DRG neurons during chronic inflammation, GT expression and therefore glutamate levels can be reduced, thereby reducing nociceptive responses.

Once NGF or other signals reach the DRG neuronal cell body, long term regulation of GT activity can be altered. The long-term regulation of GT activity is controlled by the amount of GT produced and has been best studied in the kidney [Curthoys and Watford, 1995]. During chronic acidosis, GT activity increases within 24 hours and remains elevated for weeks after reaching a plateau at 7 days [Curthoys and Lowry, 1973]. This occurs by an increase in the amount of GT and not activation of the preexisting enzyme [Curthoys et al., 1976; Curthoys and Watford, 1995]. The rate of GT transcription is unaffected by these conditions, but the level of total and translatable GT mRNA is increased by stabilization of GT mRNA [Tong et al., 1987; Curthoys and Watford, 1995; Curthoys and Gstraunthaler, 2001]. Stabilization occurs by the binding of a cytosolic protein to an eight-base AU sequence repeat within the 3'-nontranslated region of the GT mRNA [Hansen et al., 1996; Laterza et al., 1997; Laterza and Curthoys, 2000; Porter et al., 2002]. This stabilizing protein is zeta-crystallin: quinone oxidoreductase [ZC; Tang and Curthoys, 2001; Curthoys and Gstraunthaler, 2001]. Since nervous system GT is similar or identical to kidney GT [Curthoys and Watford, 1995; Holcomb et al., 2000], it is possible that a similar mechanism exists in primary sensory neurons. Therefore, it is important to determine the role ZC has in increased GT production in DRG neurons during chronic inflammation. Several studies have shown altered levels of ZC in diseased neurons, tumor cells, and other tissues undergoing cellular stress [Wang et al, 2000; Siegel and Ross, 2000; Schelonka et al., 2000; Wilson et al., 2001]. In the present report, ZC levels increase in the DRG neuronal cell bodies during the early stages of inflammation, preceding increases in glutaminase. Inhibition of ZC, therefore, was carried out to determine if glutaminase levels and pain behaviors could be modified.

ZC is inhibited by several classes of compounds [al-Hamidi et al., 1997; Rabbani and Duhaiman, 1998; Winski et al., 2001; Bazzi et al., 2002]. Dicoumarol [DC] is a potent, competitive inhibitor of ZC, binding to the pyridine nucleotide site [Hollander and Ernster, 1975; Hosada et al., 1974, Jaiswal, 2000] and has been used as the traditional inhibitor of ZC in many studies [Cross et al., 1999; Winski et al., 2001]. Therefore, DC was administered to DRG neuronal cell bodies during chronic inflammation to disrupt ZC's regulation of GT production. The administration of DC caused a decrease in ZC and GT levels, as well as reducing nociceptive responses such as thermal hyperalgesia and mechanical allodynia.

Inhibition of Glutaminase Activity.

Cutaneous primary afferents are classified into three general categories and proportions: 1. small diameter, unmyelinated, slow conducting C fibers [70%]; 2. medium diameter, lightly myelinated, intermediate conducting Adelta fibers [$10$%]; 3. large diameter, myelinated, fast conducting Ab fibers [20%] [Millan, 1999]. Under normal conditions, nociceptors are categorized into Adelta fibers that evoke a rapid, acute pain sensation and C fibers that produce a later, 'dull' pain [Campbell, 1987]. In acute inflammation there is a release of substances that sensitize normal peripheral primary afferents and recruit 'silent nociceptors' in an area of primary hyperalgesia, typified by increased sensitivity to mechanical, heat, and chemical stimuli. A secondary hyperalgesia in nearby undamaged areas is thought to be due to central spinal mechanisms [review, Millan, 1999].

Sensitizing substances released during acute inflammation include: 5-HT, histamine—mast cells; prosta-glandins (PG)—fibroblasts, Schwann cells; cytokines, $H^+$, nitric oxide (NO)—macrophages; ATP, $H^+$—damaged cells; 5-HT—platelets; ATP, NO—blood vessels; bradykinin, other kinins—blood; PG, neuropeptide Y, ATP—sympathetic terminals. There also is a neurogenic component of inflammation due to the release of bioactive substances from peripheral primary afferent terminals. Substance P (SP) and calcitonin gene-related peptide (CGRP) are released from stimulated terminals or via axon reflexes (collateral fibers) further sensitizing surrounding afferent terminals and tissues. These algogenic substances influence primary afferents to increase $Ca^{2+}$ and $Na^+$ permeability, decrease $K^+$ permeability, increase intracellular $Ca^{2+}$ concentration, NO and PG production, and adenylate cyclase and phospholipase C activities [Millan, 1999]. The peripheral primary terminal, therefore, is acutely sensitized producing primary hyperalgesia.

Glutamate also is involved in neurogenic inflammation. As stated earlier, a number of stimuli evoke glutamate release from nerve trunks, skin, joints, and dental pulp [Bledsoe, et al., 1980, 1989; Jackson et al., 1993; deGroot et al., 2000; Lawand et al., 2000]. Local release or administration of glutamate and EAA agonists sensitize peripheral afferents and produce acute nociceptive reflexes/hyperalgesia that can be blocked by EAA antagonists [Ault & Hildebrand, 1993a,b; Jackson et al., 1995; Zhou et al., 1996; Davidson et al., 1997; Lawand et al., 1997; Wang et al., 1997; Carlton et al., 1998; Ushida et al., 1999; Bhave et al., 2001]. Fibers of the Ab type also contain EAA receptors [Coggeshall & Carlton, 1997; Wood & Docherty, 1997] and may be involved in mechanical allodynia [Millan, 1999]. During acute inflammation, the number of glutamate-immunoreactive axons in peripheral nerve increases from 25% to 60% after several hours [Westlund et al., 1992]. This acute alteration in glutamate concentrations in peripheral primary afferents is due to local regulation of GT activity and glutamate production. The present invention shows that chronic alterations in glutamate concentrations, however, involves increased production of glutaminase in the neuronal cell bodies followed by increased amounts of glutaminase and glutamate in the peripheral nerve fibers.

Based on these studies, it is believed that increased glutamate production and release acting on elevated numbers of nerve terminals with glutamate receptors would maintain sensitization of peripheral afferents and exacerbate the process of chronic pain from the periphery. It has been shown herein that inhibition of GT via a one-time application of a GT enzyme inhibitor into the chronically inflamed field reduces nociceptive responses, such as mechanical allodynia and thermal hyperalgesia, and elevated glutamate levels during chronic inflammation for several days. Several classes of inhibitors acting at binding sites for glutamine and glutamate or at regulatory sites on glutaminase appear to be extremely effective in reducing pain responses.

In summary, it has been shown that glutamate metabolism is altered for weeks in rat primary sensory neurons during chronic inflammation. Elevated levels of glutamate and glutaminase (GT), its synthetic enzyme, occur in the neuronal cell bodies of dorsal root ganglia (DRG) followed by increases in the peripheral afferents of skin and joints. Chronic increase in production and release of glutamate can stimulate glutamate receptors on sensory afferents to produce hyperalgesia and allodynia. Therefore, elevated peripheral levels of glutamate cause exaggerated nociceptive responses during chronic inflammation. Recent studies have demonstrated that zeta-crystallin:quinone oxidoreductase (ZC) is a stabilizer of GT mRNA to increase GT levels. Also, nerve growth factor (NGF) has been shown to act as a retrograde signal from the site of inflammation to induce chronic alterations in sensory neurons. Therefore, ZC and NGF are responsible for altering GT levels in primary sensory neurons during chronic inflammation. The following conclusions can be made from the research presented herein:

(1) inhibition of GT reduces nociceptive responses and elevated glutamate levels during chronic inflammation. Inhibition of GT will be produced with a GT inhibitor at the DRG, sciatic nerve or in the inflamed paw during chronic inflammation.

(2) GT production in DRG neurons during chronic inflammation is regulated by ZC. ZC is a stabilizer of GT mRNA, allowing increased GT translation during times of cellular stress. An effective amount of a ZC inhibitor can be administered to the DRG to disrupt GT mRNA stabilization and reduce nociceptive responses during the development of chronic inflammation.

(3) glutamate metabolism in primary sensory neurons can be modified by NGF. NGF has been implicated in chronic alterations of DRG neurons. Administration of NGF to naive rats and NGF neutralization in chronic inflammation should have a similar effect as a ZC inhibitor on nociceptive behavior and glutamate metabolism in primary sensory neurons.

Materials and Methods

For the experiments described herein, adult Sprague Dawley male rats, 200–300 g, were used. One set of normal rats was used to evaluate the effects of fixation on glutaminase immunohistochemical staining and for determining antisera dilutions. For all other rats, at day 0, a limited arthritis was induced in the right hindpaw by the intraplantar subcutaneous injection of 75–150 μl of complete Freund's adjuvant (CFA; *Mycobacterium butyricum*; Sigma) emulsified in saline (1:1). Controls were naïve rats that received no injection or rats that received intraplantar injection of saline (75 μl). For peripheral glutaminase inhibition studies, the inflamed hindpaws were injected with glutaminase inhibitors (25 μl) at day 3 of inflammation. Some rats with inflammation received saline injections (25 μl) into the inflamed hindpaw at day 3. Procedures in this study were conducted according to guidelines from the International Association for the Study of Pain [Zimmerman, 1983] and the National Institutes of Health publication #80-23 and were approved by the University of Oklahoma Health Sciences Institutional Animal Care and Use Committee. Efforts were made to minimize the number of animals used for this study.

The $L_4$ DRG was examined for the following reason. The tibial nerve, a branch of the sciatic nerve, innervates the majority of the plantar surface of the rat hindpaw [Swett and Woolf, 1985]. Approximately, 99% of the tibial DRG neuronal perikarya of rats are located in the $L_4$-$L_5$ DRG's, and the $L_4$ DRG contains more than twice the number than $L_5$ [Swett et al, 1991].

Two to three days prior to and for the days following CFA injection, rats were tested for pressure sensitivity with von Frey hairs (Semmes-Weinstein monofilaments; Stoelting, Inc.). Rats were allowed to acclimate for five to ten minutes in a plastic box (25×25×25 cm) with 6 mm holes spaced every 6 mm [Pitcher et al, 1999a,b]. Monofilaments calibrated for specific forces were inserted through the holes underneath the box to probe the plantar surface of the hindpaw, 5 times in 3–4 sec intervals in different places on the plantar surface. Filaments with light force were used first, followed by filaments of increasing force. A filament was slowly applied perpendicularly to the plantar surface until bending of the filament occurred. If the paw did not retract three out of five times, the next larger filament was used. The threshold force was defined as the filament (force) that caused the foot retraction without bending the monofilament three out of five times. Using a conversion table for the filaments, thresholds were reported as gram force.

Thermal latencies for the footpad plantar surface were determined with the Hargreaves' model (Ugo Basile, Italy). Rats were placed on an elevated glass plate (3 mm) in clear plastic boxes with air holes in the lids and allowed to acclimate for 10 minutes. Radiant heat was applied to the plantar surface of the hindpaw and the withdrawal latency recorded. A second test was followed after 5–10 minutes. All behavioral testing occurred at 21–22° C. with indirect lighting in the testing room. Differences between groups for pressure thresholds and thermal latencies were determined with a Student's t test ($p<0.05$ for significance) using InStat biological statistics program (GraphPad Software, Inc., San Diego).

For immunohistochemical localization of GT, rats at 3, 7, and 10 days (n=6 CFA/time pt; n=4 control/time pt; n=3 additional controls) were anesthetized with sodium pentobarbital (90 mg/kg) and transcardially perfused with fixative: 0.2% paraformaldehyde (PFA), 70% picric acid (PA) in 0.1M phosphate buffer, pH 7.4 [Miller et al, 1993, 2002]. Right and left $L_4$ DRG's and hindpaws were removed and placed overnight in fixative at 4° C.; the PFA concentration was increased to 2% for post-fixation [Miller et al, 1993, 2002]. Additional control rats (n=3) were perfused transcardially with 4% PFA in O.1M Sorenson's phosphate buffer, pH 7.4. DRG's were removed and placed in fixative overnight at 4° C. All tissues were transferred to $^2$0% sucrose in O.1M Sorenson's phosphate buffer, pH 7.4 for 24–96 hr at 4° C. The tissue was frozen, sectioned at 20 μm in a cryostat, thaw mounted onto gelatin coated slides, and dried for 1 hr at 37° C. Sections were washed three times for 10 min. in phosphate buffered saline (PBS) and incubated in 10% normal goat serum, 10% normal horse serum, 10% fetal bovine serum, 2% BSA, and 1% polyvinylpyrolidone in PBS with 0.3% Triton (PBS-T).

To evaluate the effects of fixation on GT immunoreactivity (IR), DRG sections from the first set of control rats (n=3 PA-PFA fixation; n=3 PFA fixation) were examined. Sections were incubated in rabbit anti-glutaminase (1:1000; gift from Dr. N. Curthoys, Colorado St. Univ., Ft. Collins, Colo.), mouse anti-glutaminase (IgM MAb 120, 1:500-5 mg/ml; gift from Dr. T. Kaneko, Kyoto Univ., Kyoto, Japan), or mouse anti-glutamate (1:3000; gift rom Dr. J. Madl, Colo. St. Univ., Ft. Collins, Colo.) in PBS-T. The tissue was washed three times in PBS and incubated in biotinylated goat anti-rabbit IgG or biotinylated goat anti-mouse IgM secondary antibody (5 μg/ml; Vector) in PBS-T for 1 hr. Some tissue sections were washed two times in PBS following secondary antibody incubation, washed in sodium carbonate buffered saline (SCBS), pH 8.5, incubated in fluorescein-avidin (1.5 mg/ml; Vector) in SCBS for 1 hr, and washed three times in PBS. Coverslips were apposed with Vectashield mounting media (Vector) to retard fading of immunofluorescence. Other sections were washed three times in PBS following secondary antibody, incubated in avidin-biotin-peroxidase (Vector), and washed three times in Tris-buffered saline, pH 7.6. Sections were incubated in diaminobenzidine (DAB) solution (0.5 mg/ml DAB, 0.003% $H_2O_2$ in Tris-saline) for 1–5 minutes. Sections were dehydrated in an ascending series of ethanols, cleared in xylenes, and coverslips were apposed with Pro-Texx (Baxter Diagnostics).

A series of dilutions (1:200–1:6000) of the rabbit antiglutaminase antiserum was used to determine an optimal dilution (1:3000) for evaluating alterations in immunohistochemical staining intensity. Also, a series of dilutions of the biotinylated goat anti-rabbit IgG secondary antiserum (1–15 μg/ml) was used to determine an optimal dilution (3

μg/ml) for this study. Tissue sections for the CFA inflammation study were incubated overnight at 4° C. in rabbit anti-glutaminase (1:3000) in PBS-T and processed for immunofluorescence as described above. Immunofluorescent and immunoperoxidase sections were observed with an Olympus Provis AX70 microscope and digital images were obtained with a SPOT™ CCD camera (Diagnostic Instruments).

DRG's were evaluated qualitatively for 3, 7 and 10 day groups, and the 7 day group was chosen for quantitative densitometric analysis. Immunofluorescent images from 7 day DRG's were captured using the CCD camera and saved as uncompressed TIFF files. Exposures were adjusted and pre-set by using experimental (CFA) images for baseline exposure. The glutaminase-immunoreactive DRG images were analyzed using the SCION Image program (Scion Co., Frederick, Md.). Individual DRG neurons were circumscribed, and the area, pixel number, and intensity were recorded. The data were recorded as intensity divided by the area of the cell. Neuronal cell bodies in the DRG were distributed into the following three sizes for analysis: 100–600 μm$^2$ (small), 600–1200 μm$^2$ (medium), and >1200 μm$^2$ (large) [Willis and Coggeshall, 1991]. Differences in the intensity per area were analyzed with ANOVA followed by a Student-Newman-Keuls post hoc test (p<0.05 for significance) using InStat biological statistics program (GraphPad Software, Inc.).

For GT enzyme assays, rats from the 7 day time point (n=6 CFA; n=4 control) were anesthetized (sodium pentobarbital, 90 mg/kg) and decapitated. Right and left L$_4$ DRG's were removed quickly, placed in embedding molds with −1 mounting media (Lipshaw), and frozen on dry ice. Individual DRG's were sectioned at −20° C. on a cryostat at 30 μm. Sections were placed in aluminum racks for lyophilization, and samples were stored under vacuum at −20° C. The embedding media was removed from around the lyophilized DRG sections using a Wild Heerbrugg type 181300 dissecting microscope, and DRG sections were weighed using quartz-fiber balances.

Enzyme assays for GT were performed according to the method of Curthoys and Lowry (1973). Five to six randomly selected sections of right and left DRG from rats with CFA and from control rats were placed individually in a 40 μl volume of reaction mixture containing: 20 mM glutamine, 100 mM K$_2$HPO$_4$, 0.6 mM EDTA, 0.01% Triton-X 100, 0.01% BSA in 50 mM TRIS, pH 8.65, for 45 minutes at 37° C. The reaction was stopped by adding 20 μl of 0.7 N HCl and placing the samples at 4° C. A volume of 1 ml of indicator buffer containing 300 μM ADP, 360 μM NAD, 50 μg/ml glutamate dehydrogenase (GDH, rat liver, Boehringer Mannheim, Indianapolis, Ind.) in 50 mM TRIS, pH 8.5 was added for 20 minutes at room temperature. In this reaction, glutamate produced by GT is converted to 2-oxoglutarate via GDH with the formation of NADH. Reduction of NAD$^+$ was measured using a fluorometer (Farrand Inc.) with an excitation wavelength of 365 nm and emission at 340 nm. Quantitation of NADH production was accomplished by reacting multiple concentrations of glutamate standards in the indication reaction. The GT activity from each DRG section was ascertained and a mean activity for each DRG was determined. Differences in GT activity from the left and right L$_4$ DRG's of CFA rats and L$_4$ DRG's from control rats were analyzed with ANOVA followed by a Student-Newman-Keuls post hoc test (p<0.05 for significance) using InStat biological statistics program (GraphPad Software, Inc.).

REFERENCES

The following references, to the extent that they provide exemplary procedural or other details supplementary to those set forth herein, are specifically incorporated herein by reference.

M. Ahmed, A. Bjurholm, M. Schultzberg, E. Theodorsson, and A. Kreicbergs, Increased levels of substance P and calcitonin gene-related peptide in rat adjuvant arthritis. A combined immunohistochemical and radioimmunoassay analysis. Arthritis Rheum. 38 (1995) 699–709.

A. A. al-Hamidi, Riskuwa A S, Ali S D (1997) Inhibition of camel lens zeta-crystallin/NADPH:quinone oxidoreductase activity by chloranilic acid. Biochem Mol Biol Int 41:415–421.

B. Ault and L. M. Hildebrand, L-glutamate activates peripheral nociceptors. Agents Actions 39 (1993a) C142–144.

B. Ault and L. M. Hildebrand, Activation of nociceptive reflexes by peripheral kainate receptors. J. Pharmacol. Exp. Ther. 265 (1993b) 927–932.

G. Battaglia and A. Rustioni, Coexistence of glutamate and substance P in dorsal root ganglion neurons of the rat and monkey. J. Comp. Neurol. 277 (1988) 302–312.

M. D. Bazzi, Rabbani N. Duhaiman A S (2002) Sequential inactivation of zeta-crystallin by o-phthalaldehyde. Biochim Biophys Acta 1597:67–73.

J. M. Besson and G. Guilbaud, The Arthritic Rat as a Model of Chronic Pain? Elsevier, Amsterdam, 1988.

J. M. Besson, The neurobiology of pain. Lancet (1999) 353:1610–1615.

G. Bhave, Karim F, Carlton S M, Gereau R W 4th (2001) Peripheral group I metabotropic glutamate receptors modulate nociception in mice. Nat Neurosci. 4:417–423.

S. C. Bledsoe, Jr., R. P. Bobbin, R. Thalmann, and I. Thalmann, Stimulus-induced release of endogenous amino acids from skins containing the lateral-line organ in *Xenopus laevis*. Exp. Brain Res. (1980) 40:97–101.

H. F. Bradford, Ward H K, Foley P (1989) Glutaminase inhibition and the release of neurotransmitter glutamate from synaptosomes. Brain Res 476:29–34.

S. Bröer, Brookes N (2001) Transfer of glutamine between astrocytes and neurons. J Neurochem 77:705–719.

G. Burnstock, A unifying purinergic hypothesis for the initiation of pain. Lancet (1996) 347:1604–1605.

L. Calzà, M. Pozza, M. Zanni, C. U. Manzini, E. Manzini, and T. Hokfelt, Peptide plasticity in primary sensory neurons and spinal cord during adjuvant-induced arthritis in the rat: An immunocytochemical and in situ hybridization study. Neuroscience (1998) 82:575–589.

A. A. Cameron, J. D. Leah, and P. J. Snow, The electrophysiological and morphological characteristics of feline dorsal root ganglion cells. Brain Res. (1986) 362:1–6.

J. N. Campbell (1987) Peripheral neural mechanisms of nociception. In The Textbook of Pain, P. D. Wall, R. Melzack, Churchill-Livingstone.

C. B. Cangro, P. M. Sweetnam, J. H. Neale, W. G. Haser, and N. P. Curthoys, Selective localization of glutaminase in spinal and sensory nerve cells. A potential marker for glutamate neurotransmission. JAMA (1984) 251:797.

C. B. Cangro, P. M. Sweetnam, J. R. Wrathall, W. G. Haser, N. P. Curthoys, and J. H. Neale, Localization of elevated glutaminase immunoreactivity in small DRG neurons. Brain Res. (1985) 336:158–161.

S. M. Carlton, G. L. Hargett, and R. E. Coggeshall, Localization and activation of glutamate receptors in unmyelinated axons of rat glabrous skin. Neurosci. Lett. (1995) 197:25–28.

S. M. Carlton, S. Zhou, and R. E. Coggeshall, Evidence for the interaction of glutamate and NK1 receptors in the periphery. Brain Res. (1998) 790:160–169.

S. M. Carlton and R. E. Coggeshall, Inflammation-induced changes in peripheral glutamate receptor populations. Brain Res. (1999) 820:63–70.

R. E. Coggeshall and S. M. Carlton, Ultrastructural analysis of NMDA, AMPA, and kainate receptors on unmyelinated and myelinated axons in the periphery. J. Comp. Neurol. (1998) 391:78–86.

F. Conti, Minelli A (1994) Glutamate immunoreactivity in rat cerebral cortex is reversibly abolished by 6-diazo-5-oxo-L-norleucine (DON), an inhibitor of phosphate-activated glutaminase. J Histo Cytochem 42:717–726.

J. V. Cross, Deak J C, Rich E A, Qian Y, Lewis M, Parrott L A, Mochida K, Gustafson D, Vande Pol S, Templeton D J (1999) Quinone reductase inhibitors block SAPK/JNK and NFkappaB pathways and potentiate apoptosis. J Biol Chem 274:31150–31154.

N. P. Curthoys and O. H. Lowry, The distribution of glutaminase isoenzymes in the various structures of the nephron in normal, acidotic, and alkalotic rat kidney. J. Biol. Chem. (1973) 248:162–168.

N. P. Curthoys, Kuhlenschmidt T, Godfrey S S, Weiss R F (1976) Phosphate-dependent glutaminase from rat kidney. Cause of increased activity in response to acidosis and identity with glutaminase from other tissues. Arch Biochem Biophys 172:162–167.

N. P. Curthoys and M. Watford Regulation of glutaminase activity and glutamine metabolism. Annu. Rev. Nutr. (1995) 15:133–159.

N. P. Curthoys, Gstraunthaler G (2001) Mechanism of increased renal gene expression during metabolic acidosis. Am J Physiol Renal Physiol 281:F381–390.

E. M. Davidson, R. E. Coggeshall, and S. M. Carlton, Peripheral NMDA and non-NMDA glutamate receptors contribute to nociceptive behaviors in the rat formalin test. Neuroreport (1997) 8:941–946.

S. De Biasi and A. Rustioni, Glutamate and substance P coexist in primary afferent terminals in the superficial laminae of spinal cord. Proc. Natl. Acad. Sci. U.S.A. (1988) 85:7820–7824.

J. deGroot, Zhou S, Carlton S M (2000) Peripheral glutamate release in the hindpaw following low and high intensity sciatic stimulation. Neuroreport 11:497–502.

A. H. Dickenson, Central acute pain mechanisms. Ann. Med. (1995) 27:223–227.

L. F. Donaldson, A. J. Harmar, D. S. McQueen, and J. R. Seckl, Increased expression of preprotachykinin, calcitonin gene-related peptide, but not vasoactive intestinal peptide messenger RNA in dorsal root ganglia during the development of adjuvant monoarthritis in the rat. Brain Res. Mol. Brain Res. (1992) 16:143–149.

I. R. Duce and P. Keen, Selective uptake of [$^3$H]glutamine and [$^3$H]glutamate into neurons and satellite cells of dorsal root ganglia in vitro. Neuroscience (1983) 8:861–866.

M. Erecinska, M. M. Zaleska, D. Nelson, I. Nissim, and M. Yudkoff, Neuronal glutamine utilization: glutamine/glutamate homeostasis in synaptosomes. J. Neurochem. (1990) 54:2057–2069.

D. Fell, Understanding the Control of Metabolism. In: K. Snell, (Series Ed.) Frontiers of Medicine Series. Portland Press, London and Miami, 1997, pp 101–193, 225–252.

F. Fonnum (1991) Neurochemical studies on glutamate-mediated neurotransmission. in *Excitatory Amino Acids*, B S Meldrum, F Moroni, R P Simon, J H Woods, eds, pp 15–25, Raven Press, New York.

E. M. Fykse, Fonnum F (1996) Amino acid neurotransmission: dynamics of vesicular uptake. Neurochem Res 21:1053–1060.

N. E. Garrett, B. L. Kidd, S. C. Cruwys, and D. R. Tomlinson, Changes in preprotachykinin mRNA expression and substance P levels in dorsal root ganglia of monoarthritic rats: comparison with changes in synovial substance P levels. Brain Res. (1995) 675:203–207.

M. G. Garry, K. E. Miller, and V. S. Seybold, Lumbar dorsal root ganglia of the cat: a quantitative sudy of peptide immunoreactivity and cell size. J. Comp. Neurol. (1989) 284:36–47.

P. G. Genever, S. J. Maxfield, G. D. Kennovin, J. Maltman, C. J. Bowgen, M. J. Raxworthy, and T. M Skerry, Evidence for a novel glutamate-mediated signaling pathway in keratinocytes. J. Invest. Dermatol. (1999) 112:337–342.

H. J. Gould, 3rd, J. D. England, Z. P. Liu, and S. R. Levinson, Rapid sodium channel augmentation in response to inflammation induced by complete Freund's adjuvant. Brain Res. (1998) 802:69–74.

L. T. Graham, Jr and M. H. Aprison, Distribution of some enzymes associated with the metabolism of glutamate, aspartate, gamma-aminobutyrate and glutamine in cat spinal cord. J. Neurochem. (1969) 16:559–566.

G. Gstraunthaler, T. Holcomb, E. Feifel, W. Liu, N. Spitaler, and N. P. Curthoys, Differential expression and acid-base regulation of glutaminase mRNAs in LLC-PK(1)-FBPase(+) cells. Am. J. Physiol. Renal Physiol. (2000) 278: F227–237.

U. Hanesch, U. Pfrommer, B. D. Grubb, B. Heppelmann, and H. G. Schaible, The proportion of CGRP-immunoreactive and SP-mRNA containing dorsal root ganglion cells is increased by a unilateral inflammation of the ankle joint of the rat. Regul. Pept. (1993) 46:202–203.

U. Hanesch, F. Blecher, R. U. Stiller, P. C. Emson, B. Heppelmann, and H. G. Schaible, The effect of unilateral inflammation at the rat's ankle joint on the expression of preprotachykinin-A mRNA and preprosomatostatin mRNA in dorsal root ganglion cells—a study using non-radioactive in situ hybridization. Brain Res. (1995) 700:279–284.

W. R. Hansen, N. Barsic-Tress, L. Taylor, and N. P. Curthoys, The 3'-nontranslated region of rat renal glutaminase mRNA contains a pH-responsive stability element. Am. J. Physiol. (1996) 271:F126–131.

K. Hargreaves, R. Dubner, F. Brown, C. Flores, and J. Joris, A new and sensitive method for measuring thermal nociception in cutaneous hyperalgesia. Pain (1988) 32:77–88.

A. A. Harper and S. N. Lawson, Conduction velocity is related to morphological cell type in rat dorsal root ganglion neurones. J. Physiol. (1985) 359:31–46.

T. Holcomb, L. Taylor, J. Trohkimoinen, and N. P Curthoys, Isolation, characterization and expression of a human brain mitochondrial glutaminase cDNA. Brain Res. Mol. Brain Res. (2000) 76:56–63.

P. M. Hollander, Ernster L (1975) Studies on the reaction mechanism of DT diaphorase. Action of dead-end inhibitors and effects of phospholipids. Arch Biochem Biophys 169: 560–567.

S. Hosoda, Nakamura W, Hayashi K (1974) Properties and reaction mechanism of DT diaphorase from rat liver. J Biol Chem 249:6416–6423.

M. J. Iadarola, J. Douglass, O. Civelli, and J. R. Naranjo, Differential activation of spinal cord dynorphin and enkephalin neurons during hyperalgesia: evidence using cDNA hybridization. Brain Res. (1988) 455:205–212.

D. L. Jackson, L. M. Aanonsen, J. D. Richardson, H. Geier, and K. M. Hargreaves, An evaluation of the effects of excitatory amino acids in bovine dental pulp. Proc. Soc. Neurosci. (1993) 19:996.

D. L. Jackson, C. B. Graff, J. D. Richardson, and K. M. Hargreaves, Glutamate participates in the peripheral modulation of thermal hyperalgesia in rats. Eur. J. Pharmacol. (1995) 284:321–325.

A. K. Jaiswal (2000) Characterization and partial purification of microsomal NAD(P)H:quinone oxidoreductases. Arch Biochem Biophys 375:62–68.

T. Kaneko, Hanazawa A, Mizuno N (1992) Enhancement of glutaminase-like immunoreactivity in rat brain by an irreversible inhibitor of the enzyme. Brain Res Bull 28:897–907.

M. Koltzenburg, Bennett D L, Shelton D L, McMahon S B (1999) Neutralization of endogenous NGF prevents the sensitization of nociceptors supplying inflamed skin. Eur J Neurosci 11:1698–1704.

E. Kvamme, Torgner I A (1975) Regulatory effects of fatty acylcoenzyme A derivatives on phosphate-activated pig brain and kidney glutaminase in vitro. Biochem J. 149:83–91.

E. Kvamme and B. E. Olsen, Evidence for two species of mammalian phosphate-activated glutaminase having different regulatory properties. FEBS Lett. (1979) 107:33–36.

E. Kvamme, Lenda K, Regulation of glutaminase by exogenous glutamate, ammonia and 2-oxoglutarate in synaptosomal enriched preparation from rat brain. Neurochem Res (1982) 7:667–78.

E. Kvamme, G. Svenneby, and I. A. Torgner, Calcium stimulation of glutamine hydrolysis in synaptosomes from rat brain. Neurochem. Res. (1983) 8:25–38.

E. Kvamme, Torgner I A, Roberg B., Evidence indicating that pig renal phosphate-activated glutaminase has a functionally predominant external localization in the inner mitochondrial membrane. J Biol Chem (1991) 266:13185–13192.

E. Kvamme, Synthesis of glutamate and its regulation. Prog. Brain Res. (1998) 116:73–85.

O. F. Laterza, W. R. Hansen, L. Taylor, and N. P. Curthoys, Identification of an mRNA-binding protein and the specific elements that may mediate the pH-responsive induction of renal glutaminase mRNA. J. Biol. Chem. (1997) 272:22481–22488.

O. F. Laterza and N. P. Curthoys, Specificity and functional analysis of the pH-responsive element within renal glutaminase mRNA. Am. J. Physiol. Renal Physiol. (2000) 278:F970–977.

N. B. Lawand, W. D. Willis, and K. N. Westlund, Excitatory amino acid receptor involvement in peripheral nociceptive transmission in rats. Eur. J. Pharmacol. (1997) 324:169–177.

N. B. Lawand, T. McNearney, and K. N. Westlund, Amino acid release into the knee joint: key role in nociception and inflammation. Pain (2000) 86:69–74.

O. H. Lowry and J. V. Passonneau, in: A Flexible System of Enzymatic Analysis, 1st Edition, Academic Press, London, 1972, pp 220–260.

M. Malcangio, Garrett N E, Tomlinson D R (1997) Nerve growth factor treatment increases stimulus-evoked release of sensory neuropeptides in the rat spinal cord. Eur J Neurosci 9:1101–1104.

L. Marlier, P. Poulat, N. Rajaofetra, and A. Privat, Modifications of serotonin, substance P and calcitonin gene-related peptide-like immunoreactivities in the dorsal horn of the spinal cord of arthritic rats: a quantitative immunocytochemical study. Exp. Brain Res. (1991) 83:482–490.

D. B. McDougal Jr., M. J. C. Yu, P. D. Gorin, and E. M. Johnson Jr., Transported enzymes in sciatic nerve and sensory ganglia of rats exposed to maternal antibodies against nerve growth factor. J.Neurochem. (1981) 6:1847–1852.

A. Merighi, J. M. Polak, and D. T Theodosis, Ultrastructural visualization of glutamate and aspartate immunoreactivities in the rat dorsal horn, with special reference to the co-localization of glutamate, substance P, and calcitonin gene-related peptide. Neuroscience (1991) 160:113–116.

M. J. Millan, The induction of pain: An integrative review. Prog. Neurobiol. (1999) 57:1–164.

K. E. Miller, V. D. Douglas, and T. Kaneko, Glutaminase immunoreactive neurons in the rat dorsal root ganglion contain calcitonin gene-related peptide (CGRP). Neurosci. Lett. (1993) 160:113–116.

K. E. Miller, R. M. Kriebel, M. J. Chandler, C. D. Ross, and R. D. Foreman, Glutamate- and glutaminase-immunoreactive nerve fibers in rat skin following peripheral inflammation. Proc. Soc. Neurosci. (1999a) 25:685.

K. E. Miller, Akesson E, Seiger A, Nerve growth factor-induced stimulation of dorsal root ganglion/spinal cord co-grafts in oculo: enhanced survival and growth of CGRP-immunoreactive sensory neurons. Cell Tissue Res (1999b) 298:243–253.

K. E. Miller, S. R. Caire, R. W. Dennis, M. J. Chandler, R. D. Foreman, R. M. Kriebel, Effects of Nerve Growth Factor (NGF) on Glutamate Metabolism in Rat Primary Sensory Neurons. Proc. Soc. Neurosci. 2001.

K. E. Miller, B. A. Richards, and R. M. Kriebel, Glutamine-, glutamine synthetase-, glutamate dehydrogenase- and pyruvate carboxylase-immunoreactivities in the rat dorsal root ganglion and peripheral nerve. Brain Res. (2002a) 945:202–211.

K. E. Miller, B. A. Richards, S. Hopkins, R. M. Kriebel, and R. D. Foreman, Increases in glutamate- and glutaminase-immunoreactivity in rat primary afferent peripheral terminals following inflammation. Neuroscience (2002b) submitted.

H. Mulder, Y. Zhang, N. Danielsen, and F. Sundler, Islet amyloid polypeptide and calcitonin gene-related peptide expression are upregulated in lumbar dorsal root ganglia after unilateral adjuvant-induced inflammation in the rat paw. Brain Res. Mol. Brain Res. (1997) 50:127–135.

H. Mulder, H. Jongsma, Y. Zhang, S. Gebre-Medhin, F. Sundler, and N. Danielsen, Pituitary adenylate cyclase-activating polypeptide and islet amyloid polypeptide in primary sensory neurons: functional implications from plasticity in expression on nerve injury and inflammation. Mol. Neurobiol. (1999) 19:229–253.

R. L. Nahin and M. R. Byers, Adjuvant-induced inflammation of rat paw is associated with altered calcitonin gene-related peptide immunoreactivity within cell bodies and peripheral endings of primary afferent neurons. J. Comp. Neurol. (1994) 349:475–485.

R. S. Nicholas, Winter J, Wren P, Bergmann R, Woolf C J (1999) Peripheral inflammation increases the capsaicin sensitivity of dorsal root ganglion neurons in a nerve growth factor-dependent manner. Neuroscience 91:1425–1433.

K. Noguchi, Y. Morita, H. Kiyama, K. Ono, and M. Tohyama, A noxious stimulus induces the preprotachykinin-A gene expression in the rat dorsal root ganglion: a quantitative study using in situ hybridization histochemistry. Molec. Brain Res. (1988) 4:31–35.

G. M. Pitcher, J. Ritchie, and J. L Henry, Paw withdrawal threshold in the von Frey hair test is influenced by the surface on which the rat stands. J. Neurosci. Methods (1999) 87:185–193.

G. M. Pitcher, J. Ritchie, and J. L. Henry, Nerve constriction in the rat: model of neuropathic, surgical and central pain. Pain (1999) 83:37–46.

S. Pockett, Spinal cord synaptic plasticity and chronic pain. Anesth. Analg. (1995) 80:173–179.

L. D. Porter, Ibrahim H, Taylor L, Curthoys N P (2002) Complexity and species variation of the kidney-type glutaminase gene. Physiol Genomics 9:157–166.

N. Rabbani, Duhaiman A S (1998) Inhibition of camel lens zeta-crystallin/NADPH:quinone oxidoreductase by pyridoxal-5'-phosphate. Biochim Biophys Acta 1388:175–180.

A. Reinert, Kaske A, Mense S (1998) Inflammation-induced increase in the density of neuropeptide-immunoreactive nerve endings in rat skeletal muscle. Exp Brain Res 121:174–180.

C. N. Sang, M. P. Hostetter, R. H. Gracely, A. S. Chappell, D. D. Schoepp, G. Lee, S. Whitcup, R. Caruso, and M. B. Max, AMPA/kainate antagonist LY293558 reduces capsaicin-evoked hyperalgesia but not pain in normal skin in humans. Anesthesiology (1998) 89:1060–1067.

L. P. Schelonka, Siegel D, Wilson M W, Meininger A, Ross D (2000) Immunohistochemical localization of NQO1 in epithelial dysplasia and neoplasia and in donor eyes. Invest Ophthalmol Vis Sci 41:1617–1622.

S. P. Schneider, Perl E R (1988) Comparison of primary afferent and glutamate excitation of neurons in the mammalian spinal dorsal horn. J Neurosci 8:2062–2073.

V. S. Seybold, M. T. Galeazza, M. G. Garry, and K. M. Hargreaves, Plasticity of calcitonin gene related peptide neurotransmission in the spinal cord during peripheral inflammation. Can. J. Physiol. Pharmacol. (1995) 73:1007–1014.

Shapiro R A, Clark V M, Curthoys N P, Covalent interaction of L-2-amino-4-oxo-5-chloropentanoic acid with rat renal phosphate-dependent glutaminase. Evidence for a specific glutamate binding site and of subunit heterogeneity. J Biol Chem (1978) 253:7086–7090.

Shapiro R A, Clark V M, Curthoys N P, Inactivation of rat renal phosphate-dependent glutaminase with 6-diazo-5-oxo-L-norleucine. Evidence for interaction at the glutamine binding site. J Biol Chem. (1979) 254:2835–2838.

D. Siegel, Ross D (2000) Immunodetection of NAD(P)H:quinone oxido-reductase 1 (NQO1) in human tissues. Free Radic Biol Med 29:246–253.

S. R. Skilling, D. H. Smullin, A. J. Beitz, and A. A. Larson, Extracellular amino acid concentrations in dorsal spinal cord of freely moving rats following veratridine and nociceptive stimulation. J. Neurochem. (1988) 51:127–132.

K. A. Sluka, K. N. Westlund, Y. C. Sun, P. M. Dougherty, L. S. Sorkin, and W. D. Willis, Neural changes in acute arthritis in monkeys. III. Changes in substance P, calcitonin gene-related peptide and glutamate in the dorsal horn of the spinal cord. Brain Res. Rev. (1992) 17:29–38.

K. A. Sluka and K. N. Westlund, Spinal cord amino acid release and content in an arthritis model: the effects of pretreatment with non-NMDA, NMDA, and NK1 receptor antagonists. Brain Res. (1993) 627:89–103.

G. D. Smith, A. J. Harmar, D. S McQueen, and J. R. Seckl, Increase in substance P and CGRP, but not somatostatin content of innervating dorsal root ganglia in adjuvant monoarthritis in the rat. Neurosci. Lett. (1992) 137:257–260.

L. S. Sorkin, K. N. Westlund, K. A. Sluka, P. M. Dougherty, and W. D. Willis, Neural changes in acute arthritis in monkeys. IV. Time course of amino acid release into the lumbar dorsal horn. Brain Res. Rev. (1992) 17:39–50.

I. Stoyanova, A. Dandov, N. Lazarov, and C. Chouchkov, GABA- and glutamate-immunoreactivity in sensory ganglia of cat: a quantitative analysis. Arch. Physiol. Biochem. (1998) 106:362–369.

J. E. Swett and C. J. Woolf, The somatotopic organization of primary afferent terminals in the superficial laminae of the dorsal horn of the rat spinal cord. J. Comp. Neurol. (1985) 231:66–77.

J. E. Swett, Y. Torigoe, V. Elie, C. Bourassa, and P. Miller, Sensory neurons of the rat sciatic nerve. Exp. Neurol. (1991) 114:82–103.

S. Tate, S. Benn, C. Hick, D. Trezise, V. John, R. J. Mannion, M. Costigan, C. Plumpton, D. Grose, Z. Gladwell, G. Kendall, K. Dale, C. Bountra, and C. J. Woolf, Two sodium channels contribute to the TTX-R sodium current in primary sensory neurons. Nat. Neurosci. (1998) 1:653–655.

A. Tang, Curthoys N P (2001) Identification of zeta-crystallin/NADPH:quinone reductase as a renal glutaminase mRNA pH response element-binding protein. J Biol Chem 276:21375–21380.

J. Tong, Shapiro R A, Curthoys N P (1987) Changes in the levels of translatable glutaminase mRNA during onset and recovery from metabolic acidosis. Biochemistry 26:2773–2777.

L. Urban, S. W. N. Thompson, and A. Dray, Modulation of spinal excitability: co-operation between neurokinin and excitatory amino acid neurotransmitters. Trends Neurosci. (1994) 17:432–437.

T. Ushida, Tani T, Kawasaki M, Iwatsu O, Yamamoto H (1999) Peripheral administration of an N-methyl-D-aspartate receptor antagonist (MK-801) changes dorsal horn neuronal responses in rats. Neurosci Lett 260:89–92.

A. Wanaka, Y. Shiotani, H. Kiyama, T. Matsuyama, T. Kamada, S. Shiosaka, and M. Tohyama, Glutamate-like immunoreactive structures in primary sensory neurons in the rat detected by a specific antiserum against glutamate. Exp. Brain Res. (1987) 65:691–694.

H. Wang, R. J. Liu, R. X. Zhang, and J. T Qiao, Peripheral NMDA receptors contribute to activation of nociceptors: a c-fos expression study in rats. Neurosci. Lett. (1997) 221:101–104.

Y. Wang, Santa-Cruz K, DeCarli C, Johnson J A (2000) NAD(P)H:quinone oxidoreductase activity is increased in hippocampal pyramidal neurons of patients with Alzheimer's disease. Neurobiol Aging 21:525–531.

D. Weinreich and R. Hammerschlag, Nerve impulse-enhanced release of amino acids from non-synaptic regions of peripheral and central nerve trunks of bullfrog. Brain Res. (1975) 84:137–142.

K. N. Westlund, Y. C. Sun, K. A. Sluka, P. M. Dougherty, L. S. Sorkin, and W. D. Willis, Neural changes in acute arthritis in monkeys. II. Increased glutamate immunoreactivity in the medial articular nerve. Brain Res. Rev. (1992) 17:15–27.

W. D. Willis and R. E. Coggeshall, (1991) Dorsal root ganglion cells and their processes. In: Sensory Mechanisms of the Spinal Cord, Plenum Press, New York and London, 1991, pp 47–48.

M. W. Wilson, Schelonka L P, Siegel D, Meininger A, Ross D (2001) Immunohistochemical localization of NAD (P)H:quinone oxidoreductase in conjunctival melanomas and primary acquired melanosis. Curr Eye Res 22:348–352.

S. L. Winski, Faig M, Bianchet M A, Siegel D, Swann E, Fung K, Duncan M W, Moody C J, Amzel L M, Ross D (2001) Characterization of a mechanism-based inhibitor of NAD(P)H:quinone oxidoreductase 1 by biochemical, X-ray crystallographic, and mass spectrometric approaches. Biochemistry 40:15135–15142.

J. N. Wood and R. Docherty, Chemical activators of sensory neurons. Ann. Rev. Physiol. (1997) 59:457–482.

C. J. Woolf (1996) Phenotypic modification of primary sensory neurons: the role of nerve growth factor in the production of persistent pain. Philos Trans R Soc Lond B Biol Sci 351:441–448.

L. C. Yang, M. Marsala, and T. L. Yaksh, Characterization of spinal amino acids, cirtrulline and PGE2 release after carrageenan/kaolin-induced knee joint inflammation: a chronic microdialysis study. Pain (1996) 67:345–354.

M. Zimmerman, Ethical guidelines for investigations of experimental pain in conscious animals. Pain (1983) 16:109–110.

X. Zhang, Z. O. Xu, T. J. Shi, M. Landry, K. Holmberg, G. Ju, Y. G. Tong, X. Bao, X. P. Cheng, Z. Wiesenfeld-Hallin, A. Lozano, J. Dostrovsky, and T. Hokfelt, Regulation of expression of galanin and galanin receptors in dorsal root ganglia and spinal cord after axotomy and inflammation. Ann. N. Y. Acad. Sci. (1998) 863:402–413.

S. Zhou, L. Bonasera, and S. M. Carlton, Peripheral administration of NMDA, AMPA or KA results in pain behaviors in rats. Neuroreport (1996) 7:895–900.

What is claimed is:

1. A method for alleviating chronic pain in a subject, the method comprising the steps of:
    administering an effective amount of at least one glutaminase inhibitor to a subject suffering from chronic pain at a peripheral nervous system inflammation site;
    wherein the administration of the effective amount of at least one glutaminase inhibitor results in inhibition of glutaminase in the peripheral nervous system of the subject at the peripheral nervous system inflammation site, thereby resulting in a reduction in glutamate stimulation of peripheral sensory nerve fibers, whereby a reduction in nociceptive responses at the peripheral nervous system inflammation site is observed without any resulting acute pain behavior.

2. The method of claim 1, wherein the at least one glutaminase inhibitor is an inhibitor of glutaminase enzyme activity or an inhibitor of glutaminase enzyme production.

3. The method of claim 2, wherein the at least one glutaminase inhibitor is selected from the group consisting of amidotransferase inhibitors, long chain fatty acids, 6-diazo-5-oxo-L-norleucine (DON), N-ethylmaleimide (NEM), p-chloromercuriphenylsulfonate (pCMPS), L-2-amino-4-oxo-5-chloropentoic acid, DON plus o-carbamoyl-L-serine, acivicin, azaserine, palmitoyl coenzyme A (CoA), stearoyl CoA, bromothymol blue, dicoumarol, and combinations and derivatives thereof.

4. The method of claim 1, wherein the subject is a human.

5. The method of claim 1, wherein the step of administering an effective amount of at least one glutaminase inhibitor to a subject suffering from chronic pain at a peripheral nervous system inflammation site is further defined as locally administering an effective amount of at least one glutaminase inhibitor to a subject suffering from chronic pain at the peripheral nervous system inflammation site.

6. The method of claim 1, wherein the step of administering an effective amount of at least one glutaminase inhibitor to a subject suffering from chronic pain at a peripheral nervous system inflammation site is further defined as injecting an effective amount of at least one glutaminase inhibitor to a subject suffering from chronic pain at a peripheral nervous system inflammation site.

7. The method of claim 1, wherein the step of administering an effective amount of at least one glutaminase inhibitor to a subject suffering from chronic pain at a peripheral nervous system inflammation site is further defined as topically applying an effective amount of at least one glutaminase inhibitor to a subject suffering from chronic pain at the peripheral nervous system inflammation site.

8. The method of claim 1, wherein the step of administering an effective amount of at least one glutaminase inhibitor to a subject suffering from chronic pain at a peripheral nervous system inflammation site is further defined as orally administering an effective amount of at least one glutaminase inhibitor to a subject suffering from chronic pain at the peripheral nervous system inflammation site.

9. The method of claim 8, wherein the effective amount of at least one glutaminase inhibitor is in the form of a prodrug.

10. The method of claim 8, wherein the effective amount of at least one glutaminase inhibitor demonstrates substantially no penetration across the central nervous system blood brain barrier.

11. The method of claim 1, wherein the administration of the effective amount of at least one glutaminase inhibitor results in a reduction in nociceptive responses at the site of inflammation for at least two days without any resulting acute pain behavior.

12. A method for alleviating acute and chronic pain in a subject, the method comprising the steps of:
    (i) administering an effective amount of at least one glutaminase inhibitor to a subject suffering from acute and chronic pain at a peripheral nervous system inflammation site;
    (ii) administering an effective amount of at least one compound having analgesic effects to the subject at the peripheral nervous system inflammation site;
    (iii) wherein the administration of the effective amount of at least one glutaminase inhibitor results in inhibition of glutaminase in the peripheral nervous system of the subject at the peripheral nervous system inflammation site, thereby resulting in a reduction in glutamate stimulation of peripheral sensory nerve fibers, and the administration of the effective amount of at least one compound having analgesic effects results in a decrease in nociceptive responses at the peripheral nervous system inflammation site without any resulting acute pain behavior.

13. The method of claim 12 wherein, in the step of administering an effective amount of at least one glutaminase inhibitor, the at least one glutaminase inhibitor is an inhibitor of glutaminase enzyme activity or an inhibitor of glutaminase enzyme production.

14. The method of claim 13, wherein the glutaminase inhibitor is selected from the group consisting of amidotransferase inhibitors, long chain fatty acids, 6-diazo-5-oxo-L-norleucine (DON), N-ethylmaleimide (NEM), p-chloromercuriphenylsulfonate (pCMPS), L-2-amino-4-oxo-5-chloropentoic acid, DON plus o-carbamoyl-L-serine, acivicin, azaserine, palmitoyl coenzyme A (CoA), stearoyl CoA, bromothymol blue, dicoumarol, and combinations and derivatives thereof.

15. The method of claim 12 wherein, in the step of administering an effective amount of at least one compound having analgesic effects, the at least one compound having analgesic effects is a glutamate antagonist or an inhibitor of glutamate binding to glutamate receptors on peripheral sensory nerves.

16. The method of claim 12, wherein the administration of the effective amount of at least one glutaminase inhibitor and the administration of the effective amount of at least one compound having analgesic effects results in a decrease in nociceptive responses at the site of inflammation that last for a period of at least two days without any resulting acute pain behavior.

* * * * *